US008453507B2

(12) United States Patent
Ellson et al.

(10) Patent No.: US 8,453,507 B2
(45) Date of Patent: Jun. 4, 2013

(54) ACOUSTIC ASSESSMENT OF CHARACTERISTICS OF A FLUID RELEVANT TO ACOUSTIC EJECTION

(75) Inventors: Richard N. Ellson, Palo Alto, CA (US); Mitchell W. Mutz, Palo Alto, CA (US)

(73) Assignee: Labcyte Inc., Sunnyvale, CA (US)

( * ) Notice: Subject to any disclaimer, the term of this patent is extended or adjusted under 35 U.S.C. 154(b) by 0 days.

(21) Appl. No.: 12/983,803

(22) Filed: Jan. 3, 2011

(65) Prior Publication Data

US 2012/0006106 A1 Jan. 12, 2012

Related U.S. Application Data

(60) Division of application No. 12/079,173, filed on Mar. 24, 2008, now Pat. No. 7,899,645, which is a division of application No. 11/048,285, filed on Jan. 31, 2005, now Pat. No. 7,354,141, which is a continuation-in-part of application No. 10/310,638, filed on Dec. 4, 2002, now Pat. No. 6,938,995, which is a continuation-in-part of application No. 10/010,972, filed on Dec. 4, 2001, now abandoned, said application No. 11/048,285 is a continuation-in-part of application No. 10/956,616, filed on Oct. 1, 2004, now Pat. No. 7,717,544.

(51) Int. Cl.
*G01H 5/00* (2006.01)

(52) U.S. Cl.
USPC .............................. 73/597; 73/64.53; 73/596

(58) Field of Classification Search
USPC ........................................ 73/64.53, 596, 597
See application file for complete search history.

(56) References Cited

U.S. PATENT DOCUMENTS

| | | | | |
|---|---|---|---|---|
| 4,254,660 A * | 3/1981 | Prause | | 73/597 |
| 4,805,453 A * | 2/1989 | Haynes | | 73/292 |
| 5,063,780 A * | 11/1991 | Landry et al. | | 73/622 |
| 5,115,808 A * | 5/1992 | Popovic et al. | | 600/438 |
| 5,122,818 A | 6/1992 | Elrod et al. | | |
| 5,596,508 A * | 1/1997 | Cuffe | | 702/171 |
| 5,708,191 A * | 1/1998 | Greenwood et al. | | 73/32 A |
| 5,808,636 A | 9/1998 | Stearns | | |
| 5,900,535 A * | 5/1999 | Doe | | 73/32 A |
| 6,082,181 A * | 7/2000 | Greenwood | | 73/32 A |
| 6,119,529 A * | 9/2000 | Di Marco et al. | | 73/861.68 |
| 6,584,860 B1 * | 7/2003 | Feller et al. | | 73/861.25 |
| 6,634,233 B2 * | 10/2003 | He | | 73/597 |
| 7,405,072 B2 | 7/2008 | Mutz et al. | | |

(Continued)

OTHER PUBLICATIONS

Kino, G.S., *Acoustic Waves: Devices, Imaging and Analog Signal Processing*, (Prentice-Hall, Inc., 1987), pp. 194-197.

*Primary Examiner* — David Rogers
(74) *Attorney, Agent, or Firm* — Jones Day

(57) ABSTRACT

Methods are provided for analyzing characteristics of fluids in the context of an acoustic ejection system. Such a system has a controller, an acoustic radiation generator, and a coupling medium coupling the radiation to a reservoir holding fluid. The methods can use acoustic radiation to both perturb a surface of the fluid in the reservoir and analyze the effect of the perturbation. The methods may use information about prior fluids. The methods of the invention can determine physical characteristics such as speed of sound and viscosity. The methods also include ways to determine a level of acoustic energy suitable to eject a droplet. Preferably the methods are executed automatically under control of programming of a controller of an acoustic ejection system.

19 Claims, 18 Drawing Sheets

U.S. PATENT DOCUMENTS

| | | |
|---|---|---|
| 7,717,544 B2 | 5/2010 | Stearns et al. |
| 2002/0094582 A1 | 7/2002 | Williams |
| 2003/0101819 A1* | 6/2003 | Mutz et al. ............. 73/602 |
| 2004/0050165 A1* | 3/2004 | He ........................ 73/597 |
| 2004/0093948 A1* | 5/2004 | Kelner et al. ........... 73/597 |
| 2004/0182138 A1* | 9/2004 | Greenwood et al. ..... 73/53.03 |
| 2005/0061060 A1* | 3/2005 | Gysling et al. ......... 73/32 A |
| 2005/0155416 A1* | 7/2005 | Ouellette et al. ....... 73/64.42 |

\* cited by examiner

ACOUSTIC ASSESSMENT OF CHARACTERISTICS OF A FLUID RELEVANT TO ACOUSTIC EJECTION

CROSS-REFERENCE TO RELATED APPLICATIONS

This application is a divisional of U.S. patent application Ser. No. 12/079,173, filed Mar. 24, 2008, which is a divisional of U.S. patent application Ser. No. 11/048,285, filed Jan. 31, 2005, which is a continuation-in-part of U.S. patent application Ser. No. 10/310,638, filed Dec. 4, 2002, which is a continuation-in-part of U.S. patent application Ser. No. 10/010,972, filed Dec. 4, 2001. Application Ser. No. 11/048, 285 is also a continuation-in-part of U.S. patent application Ser. No. 10/956,616, filed Oct. 1, 2004. These priority applications are incorporated herein by reference.

TECHNICAL FIELD

The invention relates generally to the use of acoustic energy to assess the contents of a plurality of reservoirs. In particular, the invention relates to devices and methods for acoustically assessing the contents of a plurality of reservoirs in order to enhance accuracy and precision in dispensing fluids from the reservoirs. The invention is particularly suited for use in conjunction with high-speed combinatorial synthetic and analytical systems that employ biomolecular libraries containing a large number of different fluid reservoirs.

BACKGROUND

The discovery of novel and useful materials depends largely on the capacity to make and characterize new compositions of matter. As a result, recent research relating to novel materials having useful biological, chemical, and/or physical properties has focused on the development and implementation of new methods and systems for synthesizing and evaluating potentially useful chemical compounds. In particular, high-speed combinatorial methods have been developed to address the general need in the art for systematic, efficient, and economical material synthesis techniques as well as methods to analyze and to screen novel materials for useful properties.

Generally, it is important to control the quality of the starting materials in any chemical synthesis process. Otherwise, the integrity of the process and the quality of the resulting product is compromised. Quality control of the starting materials is a particularly important issue in combinatorial synthesis procedures. In such procedures, for example, those employed in peptide drug discovery applications, a large number of starting compounds may be dispensed in a predetermined sequence from a compound library to synthesize a batch of a drug containing a specific peptide sequence. Should any of the starting compounds contain an unacceptable level of a contaminant or exhibit an unacceptable degree of degradation, the resulting compound may be rendered useless. In effect, all starting compounds employed for the batch synthesis would be wasted. This is particularly problematic when the one or more of the starting compounds are rare or expensive.

Similarly, combinatorial testing techniques may be employed in analytical and testing procedures. For example, a plurality of pharmacologically active candidate compounds may be delivered to a test sample in combination in order to assess whether synergistic effects are achieved. If any one of the candidate compounds is compromised in quality, however, the accuracy and reliability of the assessment may be reduced. Thus, further testing may be necessary, adding significantly to the overall time and cost associated with the combinatorial testing process.

High-speed combinatorial methods often involve the use of array technologies that require accurate dispensing of fluids each having a precisely known chemical composition, concentration, stoichiometry, ratio of reagents, and/or volume. Such array technologies may be employed to carry out various synthetic processes and evaluations, particularly those that involve small quantities of fluids. For example, array technologies may employ large numbers of different fluids to form a plurality of reservoirs that, when arranged appropriately, create combinatorial libraries. Thus, array technologies are desirable because they are commonly associated with speed and compactness.

In order to carry out combinatorial techniques, a number of fluid dispensing techniques have been explored, such as pin spotting, pipetting, inkjet printing, and acoustic ejection. Many of these techniques possess inherent drawbacks that must be addressed, however, before the fluid dispensing accuracy required for the combinatorial methods can be achieved. For instance, a number of fluid dispensing systems are constructed using networks of tubing or other fluid-transporting vessels. Tubing, in particular, can entrap air bubbles, and nozzles may become clogged by lodged particulates. As a result, system failure may occur and cause spurious results. Furthermore, cross-contamination between the reservoirs of compound libraries may occur due to inadequate flushing of tubing and pipette tips between fluid transfer events. Cross-contamination can easily lead to inaccurate and misleading results.

Acoustic ejection provides a number of advantages over other fluid dispensing technologies. In contrast to inkjet devices, nozzleless fluid ejection devices are not subject to clogging and their associated disadvantages, e.g., misdirected fluid or improperly sized droplets. Furthermore, acoustic technology does not require the use of tubing or involve invasive mechanical actions, for example, those associated with the introduction of a pipette tip into a reservoir of fluid.

Acoustic ejection has been described in a number of patents. For example, U.S. Pat. No. 4,308,547 to Lovelady et al. describes a liquid drop emitter that utilizes acoustic principles to eject droplets from a body of liquid onto a moving document to result in the formation of characters or barcodes thereon. A nozzleless inkjet printing apparatus is used such that controlled drops of ink are propelled by an acoustical force produced by a curved transducer at or below the surface of the ink. Similarly, U.S. Patent Application Publication No. 20020037579 to Ellson et al. describes a device for acoustically ejecting a plurality of fluid droplets toward discrete sites on a substrate surface for deposition thereon. The device includes an acoustic radiation generator that may be used to eject fluid droplets from a reservoir, as well as to produce a detection acoustic wave that is transmitted to the fluid surface of the reservoir to become a reflected acoustic wave. Characteristics of the reflected acoustic radiation may then be analyzed in order to assess the spatial relationship between the acoustic radiation generator and the fluid surface.

Other patents and patent documents describe the use of acoustic radiation for ejection and/or detection. For example, pool depth feedback technology using acoustic radiation is described in U.S. Pat. No. 5,520,715 to Oeftering. In addition, U.S. Patent Application Publication No. 20020094582 to Williams describes similar acoustic detection technology. Thus, acoustic ejection may provide an added advantage in that the proper use of acoustic radiation provides feedback relating to the process of acoustic ejection itself. Such feedback in turn may be employed to ensure that the acoustic radiation generator is maintained in proper relationship to a fluid surface in a reservoir for proper focus. Regardless of the dispensing technique used, however, inventory and materials handling limitations generally dictate the capacity of combinatorial methods to synthesize and analyze increasing numbers of sample materials. For instance, during the formatting and dispensing processes, microtiter plates that contain a plurality of fluids in individual wells may be thawed, and the contents of selected wells can then be extracted for use in a combinatorial method. When a pipetting system is employed during extraction, a minimum loading volume may be required for the system to function properly. Similarly, other fluid dispensing systems may also require a certain minimum reservoir volume to function properly. Thus, for any fluid dispensing system, it is important to monitor the reservoir contents to ensure that at least a minimum amount of fluid is provided. Such content monitoring generally serves to indicate the overall performance of a fluid dispensing system, as well as to maintain the integrity of the combinatorial methods.

In addition, during combinatorial synthesis or analysis processes, environmental effects may play a role in altering the reservoir contents. For example, dimethylsulfoxide (DMSO) is a common organic solvent employed to dissolve or suspend compounds commonly found in drug libraries. DMSO is highly hygroscopic and tends to absorb any ambient water with which it comes into contact. In turn, the absorption of water dilutes the concentration the compounds as well as alters the ability of the DMSO to suspend the compounds. Furthermore, the absorption of water may promote the decomposition of water-sensitive compounds.

A number of patents describe the use of acoustic energy to assess the contents of a container. U.S. Pat. No. 5,507,178 to Dam, for example, describes a sensor for determining the presence of a liquid and for identifying the type of liquid in a container. The ultrasonic sensor determines the presence of the liquid through an ultrasonic liquid presence sensing means and identifies the type of liquid through a liquid type identification means that include a pair of electrodes and an electrical pulse generating means. This device suffers from the disadvantage that the sensor must be placed in contact with the liquid.

U.S. Pat. No. 5,880,364 to Dam, on the other hand, describes a non-contact ultrasonic system for measuring the volume of liquid in a plurality of containers. An ultrasonic sensor is disposed opposite the top of the containers. A narrow beam of ultrasonic radiation is transmitted from the sensor to the open top of an opposing container to be reflected from the air-liquid interface of the container back to the sensor. By using the round trip transit time of the radiation and the dimensions of the containers being measured, the volume of liquid in the container can be calculated. This device cannot be used to assess the contents of sealed containers. In addition, the device lacks precision because air is a poor conductor of acoustic energy. Thus, while this device may provide rough estimate of the volume of liquid in relatively large containers, it is unsuitable for use in providing a detailed assessment of the contents of reservoirs typically used in combinatorial techniques. In particular, this device cannot determine the position of the bottom of containers since substantially all of the emitted acoustic energy is reflected from the liquid surface and does not penetrate to detect the bottom. Small volume reservoirs such as standard well plates are regular arrays of fluid containers, and the location of the bottoms of the containers can vary by a significant fraction of the nominal height of a container due to bow in the plate. Thus, detection of only the position of the liquid surface leads to significant errors in height and thus volume estimation in common containers.

In general, acoustic technology as applied to reservoir content assessment involves using a single acoustic generator to interrogate reservoirs successively. As discussed in U.S. Patent Application Publication Nos. 20020037579 to Ellson et al. and 20020094582 to Williams et al., a generator for generating focused acoustic radiation is placed in acoustic coupling relationship to each of the reservoirs to interrogate them in succession. Accordingly, the generator, the reservoirs, or both must be physically displaced. Such "single point" auditing systems may be of limited practical usefulness when large numbers of reservoirs are to be interrogated, because it would take too long to move the generator and/or the reservoirs. Using a plurality of such generators would increase the total cost and the complexity of a single point acoustic auditing system. In addition, such generators require additional space and are not easily incorporated into compact systems.

The process of acoustic ejection itself requires knowledge of the characteristics of the fluid to be ejected. Such characteristics include, for example, the speed of sound in that fluid. It is desirable to use acoustic radiation to determine those characteristics in a manner which is convenient for users of acoustic ejection systems.

Thus, there is a need in the art for improved methods and devices that are capable of high-speed monitoring the contents of a plurality of reservoirs, a capability that is particularly useful in synthetic and analytical processes to increase the robustness, efficiency, and effectiveness of the combinatorial techniques employed therein.

SUMMARY OF THE INVENTION

In an embodiment of the invention, there is an improved method for measuring the speed of sound in a fluid by immersing a solid object in the fluid and detecting acoustic radiation reflected from that solid object. Preferably the solid object is placed at two or more precisely known positions, and the speed of sound is calculated from the times taken to return an echo from the solid object in each of its two or more positions. This method is preferably carried out in an acoustic ejection system which typically includes a transducer providing focused acoustic radiation which can be coupled to a quantity of fluid in a reservoir.

In a further embodiment of the invention, there is a method for adjusting the parameters of a waveform for a toneburst intended to eject a droplet of a desired size. In the method a reservoir of the fluid is provided and one or more, preferably hundreds, of droplets are ejected using that toneburst into a further reservoir. Acoustic radiation is used to detect the level of fluid in the further reservoir after ejection and optionally before ejection. Preferably the further reservoir is moved automatically into position relative to the acoustic radiation generator. The change in level of fluid in the further reservoir is used to determine the droplet size, and parameters of the waveform are adjusted to change the droplet size in the direction of the desired size.

In another embodiment of the invention, the parameters of a waveform for a toneburst intended to eject droplets of a fluid of interest are interpolated or extraplated from parameters previously stored for tonebursts that achieve particular ejection volumes for other fluids. The interpolation or extrapolation is carried out by measuring characteristics of the fluid of interest and using those characteristics to interpolate or extrapolate between the previously stored parameters.

In still another embodiment of the invention, there is a method of determining a characteristic of a fluid, which comprises the steps of sending towards the vicinity of the fluid surface a toneburst of focused acoustic radiation, measuring an attribute of the fluid surface at a number of times subsequent to the arrival of the toneburst at the vicinity of the surface. Taking as an input the variation of the attribute with time, the characteristic of the fluid is computed.

In a further embodiment of the invention, the energy level suitable for ejecting a droplet from a fluid is determined by sending test pulses to the vicinity of a surface of a quantity of that fluid and examining echoes of probe pulses from the surface in the time or frequency domain.

In another embodiment of the invention, an acoustic ejection system is programmed, e.g., through software or firmware, to perform the methods of the invention. Such an acoustic ejection system encompasses a controller, an acoustic transducer, and a coupling medium for acoustically coupling the transducer to a reservoir.

The method of the invention encompasses using any of the techniques described above to assess characteristics of a plurality of fluids each in a reservoir, preferably automatically and without need for human intervention. The reservoirs holding the fluids may be integral to one structure, e.g., a well plate.

BRIEF DESCRIPTION OF THE DRAWINGS

FIG. 1A shows the acoustic ejector acoustically coupled to the first reservoir; the ejector is activated in order to eject a droplet of fluid from within the first reservoir toward a site on a substrate surface to form an array. FIG. 1B shows the acoustic ejector acoustically coupled to a second reservoir.

FIG. 3A illustrates a well plate in top view. FIG. 3B illustrates the well plate in cross-sectional view along dotted line A. FIG. 3C illustrates the well plate in bottom view.

FIGS. 6A-6D illustrates the device in side view. FIGS. 6E-6F illustrate the device in top view without the substrate.

DETAILED DESCRIPTION OF THE INVENTION

Figure 1A:
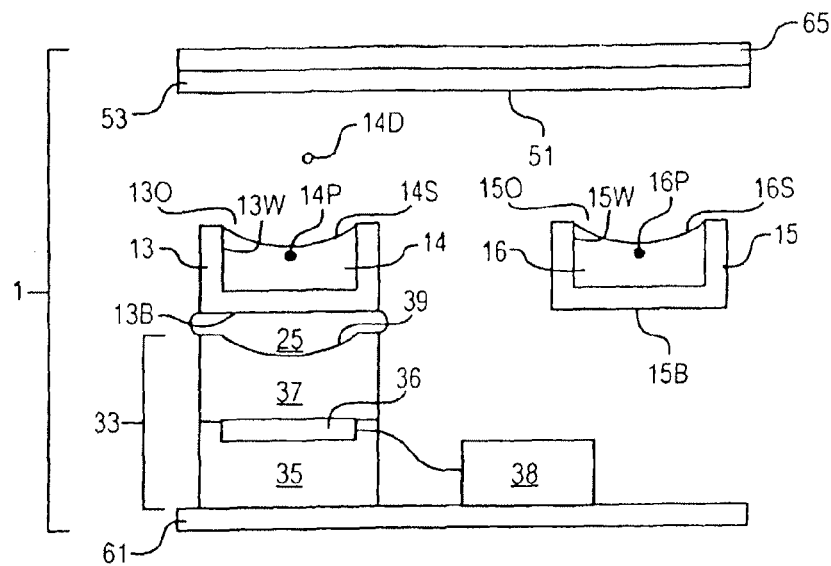
FIGS. 1A and 1B, collectively referred to as FIG. 1, schematically illustrate in simplified cross-sectional view a preferred embodiment of the inventive device that allows both the acoustic assessment in reflective mode of the contents of a plurality of reservoirs and the ejection of fluid droplets therefrom. As depicted, the device comprises first and second reservoirs, a combined acoustic analyzer and ejector, and an ejector positioning means.

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise. Thus, for example, reference to "a reservoir" includes a single reservoir as well as a plurality of reservoirs, reference to "a fluid" includes a single fluid and a plurality of fluids, reference to "a biomolecule" includes a single biomolecule and combination of biomolecules, reference to "an ejector" includes a single ejector as well as plurality of ejectors and the like.

In describing and claiming the present invention, the following terminology will be used in accordance with the definitions set forth below.

The terms "acoustic coupling" and "acoustically coupled" as used herein refer to a state wherein an object is placed in direct or indirect contact with another object so as to allow acoustic radiation to be transferred between the objects without substantial loss of acoustic energy. When two entities are indirectly acoustically coupled, an "acoustic coupling medium" is needed to provide an intermediary through which acoustic radiation may be transmitted. Thus, an ejector may be acoustically coupled to a fluid, such as by immersing the ejector in the fluid, or by interposing an acoustic coupling medium between the ejector and the fluid, in order to transfer acoustic radiation generated by the ejector through the acoustic coupling medium and into the fluid.

The term "attached," as in, for example, a substrate surface having a moiety "attached" thereto, includes covalent and noncovalent binding, adsorption, and physical immobilization. The terms "binding" and "bound" are identical in meaning to the term "attached."

The term "array" as used herein refers to a two-dimensional arrangement of features, such as an arrangement of reservoirs (e.g., wells in a well plate) or an arrangement of different moieties, including ionic, metallic, or covalent crystalline, e.g., molecular crystalline, composite or ceramic, glassine, amorphous, fluidic or molecular materials on a substrate surface (as in an oligonucleotide or peptidic array). Arrays are generally comprised of regular, ordered features, as in, for example, a rectilinear grid, parallel stripes, spirals, and the like, but non-ordered arrays may be advantageously used as well. In particular, the term "rectilinear array" as used herein refers to an array that has rows and columns of features wherein the rows and columns typically, but not necessarily, intersect each other at a ninety-degree angle. An array is distinguished from the more general term "pattern" in that patterns do not necessarily contain regular and ordered features. An array is distinguished from the more general term "pattern" in that patterns do not necessarily contain regular and ordered features.

The terms "biomolecule" and "biological molecule" are used interchangeably herein to refer to any organic molecule that is, was, or can be a part of a living organism, regardless of whether the molecule is naturally occurring, recombinantly produced, or chemically synthesized in whole or in part. The terms encompass, for example, nucleotides, amino acids, and monosaccharides, as well as oligomeric and polymeric species, such as oligonucleotides and polynucleotides, peptidic molecules, such as oligopeptides, polypeptides and proteins, saccharides such as disaccharides, oligosaccharides, polysaccharides, mucopolysaccharides or peptidoglycans (peptidopolysaccharides) and the like. The terms also encompass ribosomes, enzyme cofactors, pharmacologically active agents, and the like. Additional information relating to the term "biomolecule" can be found in U.S. Patent Application Publication No. 20020037579 to Ellson et al.

The term "fluid" as used herein refers to matter that is nonsolid, or at least partially gaseous and/or liquid, but not entirely gaseous. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous.

The terms "focusing means" and "acoustic focusing means" refer to a means for causing acoustic waves to converge at a focal point, either by a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as are known in the art and described, for example, in U.S. Pat. No. 5,798,779 to Nakayasu et al. and Amemiya et al. (1997) *Proceedings of the 1997 IS&T NIP13 International Conference on Digital Printing Technologies*, pp. 698-702.

The term "image field" refers to a region interrogated by acoustic radiation from an acoustic radiation generator without relative movement between the generator and the region. For example, when an acoustic radiation generator is used to generate acoustic radiation that allows for the interrogation of an entire row of reservoirs at one time in a rectilinear reservoir array, the image field is comprised of the row of reservoirs under interrogation. Thus the image field associated with an acoustic radiation generator is dependent on the particular generator used and the spatial relationship between the generator and the region. For example, acoustic radiation generators having electronic beam steering and/or focusing may be associated with a variable image field depending on the particular steering and/or focusing employed. In contrast, a single nonadjustable focused acoustic transducer in fixed alignment with a region of an item is associated with an invariable image field.

The terms "library" and "combinatorial library" are used interchangeably herein to refer to a plurality of chemical or biological moieties arranged in a pattern or an array such that the moieties are individually addressable. In some instances, the plurality of chemical or biological moieties is present on the surface of a substrate, and in other instances, the plurality of moieties represents the contents of a plurality of reservoirs. Preferably, but not necessarily, each moiety is different from each of the other moieties. The moieties may be, for example, peptidic molecules and/or oligonucleotides.

The term "moiety" refers to any particular composition of matter, e.g., a molecular fragment, an intact molecule (including a monomeric molecule, an oligomeric molecule, and a polymer), or a mixture of materials (for example, an alloy or a laminate).

"Optional" or "optionally" means that the subsequently described circumstance may or may not occur, so that the description includes instances where the circumstance occurs and instances where it does not.

The terms "pathogen" and "pathogenic" as used herein refer to any agent that is capable of causing disease and/or a toxic response in an individual. The individual may be a human, an animal (mammalian or otherwise), or on occasion, a plant. Typically, a pathogen referred to herein is a bacterium or virus, but may also be an organic toxin such as strychnine or botulinum, or an inorganic toxin such as arsenic or sodium cyanide. Thus, the term "pathogen-containing fluid" refers to nonsolid matter that is completely or partially pathogenic in nature. Such a fluid, for example, may be comprised of liquid that contains a pathogen minimally, partially, or fully solvated, dispersed, or suspended therein. Examples of pathogen-containing fluids include, without limitation, a culturing medium containing bacterial or viral infectious agents. Similarly, the term "nonpathogenic" refers to matter that is not pathogenic, i.e., any agent that is not likely to cause disease or a toxic response. Nonpathogenic particles, for example, include, without limitation, beneficial cellular matter such as lactobacilli, yeast, epidermal cells, beads, and the like. Nonpathogenic fluids include, for example, sterile saline, glucose solutions, and the like. Additional information relating to the terms "pathogen," "pathogen-containing fluids," "nonpathogenic," and the like can be found in U.S. patent application Ser. No. 10/199,907 for "Acoustic Radiation for Ejecting and Monitoring Pathogenic Fluids," filed Jul. 18, 2002, inventors Mutz and Ellson (assigned to Picoliter Inc., Sunnyvale, Calif.).

The term "radiation" is used in its ordinary sense and refers to emission and propagation of energy in the form of a waveform disturbance traveling through a medium such that energy is transferred from one particle of the medium to another without causing any permanent displacement of the medium itself. Thus, radiation may refer, for example, to electromagnetic waveforms as well as acoustic vibrations.

Accordingly, the terms "acoustic radiation" and "acoustic energy" are used interchangeably herein and refer to the emission and propagation of energy in the form of sound waves. As with other waveforms, acoustic radiation may be focused using a focusing means, as discussed below. Although acoustic radiation may have a single frequency and associated wavelength, acoustic radiation may take a form, e.g. a "linear chirp," that includes a plurality of frequencies. Thus, the term "characteristic wavelength" is used to describe the mean wavelength of acoustic radiation having a plurality of frequencies.

The term "reservoir" as used herein refers to a receptacle or chamber for containing a fluid. In some instances, a fluid contained in a reservoir necessarily will have a free surface, e.g., a surface that allows acoustic radiation to be reflected therefrom or a surface from which a droplet may be acoustically ejected. A reservoir may also be a locus on a substrate surface within which a fluid is constrained.

The term "substrate" as used herein refers to any material having a surface onto which one or more fluids may be deposited. The substrate may be constructed in any of a number of forms including, for example, wafers, slides, well plates, or membranes. In addition, the substrate may be porous or nonporous as required for deposition of a particular fluid. Suitable substrate materials include, but are not limited to, supports that are typically used for solid phase chemical synthesis, such as polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, and divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses, ceramics, such substrates treated with surface coatings, e.g., with microporous polymers (particularly cellulosic polymers such as nitrocellulose), microporous metallic compounds (particularly microporous aluminum), antibody-binding proteins (available from Pierce Chemical Co., Rockford Ill.), bisphenol A polycarbonate, or the like. Additional information relating to the term "substrate" can be found in U.S. Patent Application Publication No. 200200377579 to Ellson et al.

The terms "transducer assembly" and "acoustic transducer assembly" are used interchangeably herein and refer to a collection of acoustic radiation generating elements, e.g., piezoelectric elements, which can be excited individually or in concert to produce acoustic radiation having a variety of beam characteristics such as shape, directionality, directivity, phase, and/or focusing. Typically, but not necessarily, the acoustic radiation generating elements of the transducer assembly are arranged in a closely spaced array.

The term "toneburst" is used to describe a burst of acoustic energy generated by a generator of acoustic energy, for example, a whistle, electronic speaker, or ultrasonic transducer. The burst may contain one or more gaps within it during which no acoustic energy is generated. If a generator generates acoustic energy during a time interval $[T_s, T_f]$ with possible gaps during that interval, the acoustic energy generated during any time interval $[T_1, T_2] \subseteq [T_s, T_f]$ may also be referred to as a toneburst.

The term "pulse" is used synonymously with toneburst. Among those of skill in the art, a toneburst tends to connote a longer burst of acoustic energy, while a pulse tends to connote a shorter burst. Because there is no firm boundary between the two terms, the two terms are treated as synonymous for purposes of this application.

The invention accordingly relates to devices and methods for acoustically assessing the contents of a plurality of fluid reservoirs. The inventive device includes a plurality of reservoirs, each adapted to contain a fluid, and an acoustic radiation generator for generating acoustic radiation. The inventive device also includes a means for positioning the acoustic radiation generator in an acoustically coupled relationship to each reservoir such that the acoustic radiation generated by the acoustic radiation generator is transmitted through at least a portion of each reservoir. An analyzer for analyzing a characteristic of acoustic radiation is positioned to receive the transmitted acoustic radiation.

The device may be constructed to include the reservoirs as an integrated or permanently attached component of the device. However, to provide modularity and interchangeability of components, it is preferred that device be constructed with removable reservoirs. Generally, the reservoirs are arranged in a pattern or an array to provide each reservoir with individual systematic addressability. In addition, while each of the reservoirs may be provided as a discrete or stand-alone item, in circumstances that require a large number of reservoirs, it is preferred that the reservoirs be attached to each other or represent integrated portions of a single reservoir unit. For example, the reservoirs may represent individual wells in a well plate. Many well plates suitable for use with the device are commercially available and may contain, for example, 96, 384, 1536, or 3456 wells per well plate, having a full skirt, half skirt, or no skirt. The wells of such well plates typically form rectilinear arrays. Manufactures of suitable well plates for use in the employed device include Corning, Inc. (Corning, N.Y.) and Greiner America, Inc. (Lake Mary, Fla.). However, the availability of such commercially available well plates does not preclude the manufacture and use of custom-made well plates containing at least about 10,000 wells, or as many as 100,000 to 500,000 wells, or more. The wells of such custom-made well plates may form rectilinear or other types of arrays. As well plates have become commonly used laboratory items, the Society for Biomolecular Screening (Danbury, Conn.) has formed the Microplate Standards Development Committee to recommend and maintain standards to facilitate the automated processing of small volume well plates on behalf of and for acceptance by the American National Standards Institute.

Furthermore, the material used in the construction of reservoirs must be compatible with the fluids contained therein. Thus, if it is intended that the reservoirs or wells contain an organic solvent such as acetonitrile, polymers that dissolve or swell in acetonitrile would be unsuitable for use in forming the reservoirs or well plates. Similarly, reservoirs or wells intended to contain DMSO must be compatible with DMSO. For water-based fluids, a number of materials are suitable for the construction of reservoirs and include, but are not limited to, ceramics such as silicon oxide and aluminum oxide, metals such as stainless steel and platinum, and polymers such as polyester and polytetrafluoroethylene. For fluids that are photosensitive, the reservoirs may be constructed from an optically opaque material that has sufficient acoustic transparency for substantially unimpaired functioning of the device.

In addition, to reduce the amount of movement and time needed to align the acoustic radiation generator with each reservoir or reservoir well during operation, discussed infra, it is preferable that the center of each reservoir be located not more than about 1 centimeter, more preferably not more than about 1.5 millimeters, still more preferably not more than about 1 millimeter and optimally not more than about 0.5 millimeter, from a neighboring reservoir center. These dimensions tend to limit the size of the reservoirs to a maximum volume. The reservoirs are constructed to contain typically no more than about 1 mL, preferably no more than about 1 μL, and optimally no more than about 1 nL, of fluid. To facilitate handling of multiple reservoirs, it is also preferred that the reservoirs be substantially acoustically indistinguishable.

When an array is provided, each reservoir may be individually, efficiently, and systematically addressed. Although any type of array may be employed, arrays comprised of parallel rows of evenly spaced reservoirs are preferred. Typically, though not necessarily, each row contains the same number of reservoirs. Optimally, rectilinear arrays comprising X rows and Y columns of reservoirs are employed with the invention, wherein X and Y are each at least 2. In some instances, X may be greater than, equal to, or less than Y. In addition, nonrectilinear arrays as well as other geometries may be employed. For example, hexagonal, spiral and other types of arrays may be used as well. In some instances, the invention may be employed to acoustically assess irregular patterns of reservoirs, e.g., droplets randomly located on a flat substrate surface such as those associated with a CD-ROM format. In addition, the invention may be used to perform acoustic assessment of reservoirs associated with microfluidic devices.

Generally, a single acoustic radiation generator is employed, though a plurality of acoustic radiation generators may be employed as well. All acoustic radiation generators employ a vibrational element or transducer to generate acoustic radiation. Often, a piezoelectric element is employed to convert electrical energy into mechanical energy associated with acoustic radiation. When a single acoustic radiation generator is employed, the positioning means should allow for the acoustic radiation generator to move from one reservoir to another quickly and in a controlled manner, thereby allowing fast and controlled scanning of the contents of the reservoirs. In order to ensure optimal performance, it is important to keep in mind that there are two basic kinds of motion: pulse and continuous. Pulse motion involves the discrete steps of moving an acoustic radiation generator into position, keeping it stationary while it emits acoustic energy, and moving the generator to the next position; again, using a high performance positioning means allows repeatable and controlled acoustic coupling at each reservoir in less than 0.1 second. Typically, the pulse width is very short and may enable over 10 Hz reservoir transitions, and even over 1000 Hz reservoir transitions. A continuous motion design, on the other hand, moves the acoustic radiation generator and the reservoirs continuously, although not at the same speed.

In some instances, the analyzer is positioned or situated in fixed alignment with respect to the acoustic radiation generator. In addition, means similar to that described above is provided for altering the relative position of the analyzer with respect to the reservoirs. The relative position of the analyzer and the acoustic radiation generator depends on the particular configuration of the device. In some instances, the device may be configured to operate in transmissive mode, such that the generated radiation is transmitted through the entirety of the reservoir whose contents are assessed. In such a case, the reservoir may be interposed between the acoustic radiation generator and an acoustic analyzer.

More typically, however, the device may be configured to operate in a reflective mode, such that the acoustic radiation is transmitted only through a portion the reservoir whose contents are being assessed. When more than one reservoir is simultaneously interrogated in a reflective mode, acoustic radiation may be transmitted through the reservoirs under interrogation and reflected back toward the analyzer. Thus, the analyzer may be positioned in a manner appropriate for this configuration, e.g., in order to receive reflected acoustic radiation. In any case, the acoustic radiation generator should be positioned such that generated acoustic radiation is transmitted through the portion of each reservoir most likely to contain a fluid for optimal performance. This reduces the chance that the analyzer will erroneously determine that a reservoir is empty. For example, as fluids ordinarily flow to the bottom of containers or are driven there by centrifugation, the acoustic radiation generator should be positioned such that generated acoustic radiation is transmitted through the bottom of a reservoir.

In a preferred configuration, as discussed in detail below, the analyzer is positioned to receive acoustic radiation reflected from a free surface of a fluid contained in each reservoir. Depending on the angle of reflection, the acoustic radiation generator and the analyzer may form an integrated unit. In such a configuration, the acoustic radiation generator may comprise a component common to the analyzer. The component common to the acoustic radiation generator and the analyzer may be a vibrational element that converts one form of energy into another, e.g., a piezoelectric element that converts acoustic/mechanical energy to electrical energy.

The analyzer may be constructed to perform a number of functions. For example, the analyzer may be adapted to analyze acoustic radiation to determine the volume of fluid in each reservoir. In addition, or in the alterative, the analyzer may be adapted to analyze acoustic radiation to determine a property of fluid in each reservoir. Other aspects of acoustic analysis are discussed infra.

As discussed above, the reservoirs may be constructed to reduce the amount of movement and time needed to align the acoustic radiation generator with each reservoir or reservoir well during operation. As a general matter of convenience and efficiency, it is desirable to analyze an entire library of different moieties in a relatively short amount of time, e.g., about one minute, or more preferably, about 10 seconds. Thus, the inventive method typically allows for the analysis of the contents of the reservoirs at a rate of at least about 96 reservoirs per minute. Faster analysis rates of at least about 384, 1536, and 3456 reservoirs per minute are achievable with present day technology as well. Thus, the invention can be operated to analyze the contents of each well of most (if not all) well plates that are currently commercially available. Proper implementation of the inventive method should yield a reservoir analysis rate of at least about 10,000 reservoirs per minute. Current commercially available positioning technology allows the acoustic radiation generator to be moved from one reservoir to another, with repeatable and controlled acoustic coupling at each reservoir, in less than about 0.1 second for high performance positioning means and in less than about 1 second for ordinary positioning means. A custom designed system will allow the acoustic radiation generator to be moved from one reservoir to another with repeatable and controlled acoustic coupling in less than about 0.001 second.

By analyzing acoustic radiation that has been transmitted through at least a portion of a selected reservoir, one may accurately determine the contents of the selected reservoir. For example, the assessment may involve determining the volume of fluid in the reservoir or determining a property of fluid in the reservoir. As discussed above, fluid properties that may be determined include, but are not limited to, viscosity, surface tension, acoustic impedance, solid content, and impurity content. In some instances, the assessment may involve measuring the travel time of acoustic radiation through the reservoir. In addition, or in the alternative, the assessment may involve determining the difference of acoustic radiation before and after transmission through the reservoir. For temperature-dependent properties, a temperature measurement means known in art, such as thermocouples, may be used in conjunction with such analyses. Optionally, the results of acoustic analysis performed by the acoustic analyzer may be stored. Thus, the inventive device may include, for example, a storage means comprising rewritable and/or permanent data storage media for storing the results of acoustic analysis performed by the analyzer.

Acoustic assessment as described above may be employed to improve fluid dispensing from each of a plurality of reservoirs adapted to contain a fluid. Thus, another embodiment of the invention relates to a device for dispensing fluid from each of a plurality of reservoirs adapted to contain a fluid. This device may include any of a number of known techniques for dispensing fluids involving contact-based fluid dispensing, e.g., pin spotting, pipetting, and inkjet printing, or non-contact based fluid dispensing, e.g., acoustic ejection. However, the inventive device represents a novel and nonobvious improvement over the fluid dispensing devices known in the art since it provides for enhanced accuracy and precision in fluid dispensing through the use of a means for acoustically assessing the contents of the reservoirs. The means for acoustically assessing the contents of the reservoirs is similar to the previously described device for assessing the contents of a plurality of fluid reservoirs in that it also comprises an acoustic radiation generator for generating acoustic radiation and an analyzer for analyzing a characteristic of acoustic radiation. A means for positioning the acoustic radiation generator in acoustic coupling relationship to each reservoir is used to ensure that acoustic radiation generated by the acoustic radiation generator is transmitted through at least a portion of each reservoir. Furthermore, the analyzer is positioned to receive the transmitted acoustic radiation.

Thus, in a preferred embodiment, the invention provides a device employs an acoustic radiation generator for generating acoustic radiation having an image field of a size sufficient to interrogate selected reservoirs of the plurality at one time. A means for positioning the acoustic radiation generator is provided so that the acoustic radiation generator is placed in acoustic coupling relationship to the selected reservoirs. As a result, acoustic radiation generated by the acoustic radiation generator is transmitted through an exterior surface of the plurality and the selected reservoirs. The device also includes an analyzer, which is situated in radiation receiving relationship to the acoustic radiation generator. The analyzer is adapted to analyze a characteristic of the transmitted acoustic radiation so as to assess the contents of each of the selected reservoirs.

The acoustic generator and the analyzer are used in combination to assess the contents of each of the selected reservoirs. Generally, any acoustic radiation generator may be employed as long as the effective beam of the acoustic radiation generated is sufficient to interrogate a plurality of selected reservoirs at one time. All acoustic radiation generators employ one or more vibrational elements or transducers to generate acoustic radiation. Typically, piezoelectric technology is employed to convert electrical energy into mechanical energy associated with acoustic radiation. Acoustic radiation generated by a single-element transducer tends to result in the formation of a diverging beam. Accordingly, single-element acoustic generators may be employed in conjunction with a focusing means, as described below, to produce acoustic radiation having an image field of appropriate size and focus.

Multiple element acoustic radiation generators such as transducer assemblies are preferred for enhanced resolution and analytical performance. In general, transducer assemblies are comprised of a plurality of elements that can be excited individually or in groups to produce ultrasonic beams. Acoustic waves from the individual elements may reinforce each other in a desired direction and cancel each other out in undesired directions. In addition, transducer assemblies may be used to detect echo signals for analysis. In such a case, echo signals detected by individual elements may be amplified separately before being combined into one signal for each reflector from which an echo arises. Transducer assemblies are advantageous in that they may enable electronic beam steering, electronic focusing, and beam formation.

There are four general types of transducer assemblies. Linear acoustic arrays are formed from a side-by-side arrangement of piezoelectric elements, which are typically rectangular in shape and about 120 to 250 in number. One may produce individual acoustic radiation beams by activating a group of these elements to produce a pulse that travels along a beam line that is perpendicular to the face of the transducer assembly. As the face of a linear acoustic array is generally planar, a rectangular image field may be produced. Curvilinear acoustic arrays are of the same general construction except that their faces are bowed. As a result, curvilinear acoustic arrays tend to produce trapezoidal image fields. Annular acoustic arrays are formed from a concentric arrangement of elements that operates in a similar manner to the linear and curvilinear acoustic arrays. Phased acoustic arrays, like linear acoustic arrays, are formed by a side-by-side arrangement of piezoelectric elements and typically have about 128 separate elements. Phased acoustic array elements are, however, typically narrower than the elements of linear acoustic arrays. When all elements in the phased acoustic array are activated, individual acoustic pulses may be produced that travel along a beam line that can be electronically steered in different directions. Electronic steering is typically achieved using time-delay methods known in the art.

Of the above described transducer assemblies, the phased transducer assembly is most preferred. When used in conjunction with a rectilinear array of reservoirs, the phased transducer assembly preferably generates an image field of sufficient size to interrogate at least a row of reservoirs at one time. In some instances, the phased transducer assembly may simultaneously interrogate all reservoirs of a row. In other instances, electronic steering of the acoustic radiation generated by a transducer assembly serves to scan the reservoirs in the image field successively. When the image field is not sufficiently large to interrogate the entire reservoir array at one time, the means for positioning the acoustic radiation generator serves to provide relative motion between the acoustic radiation generator and the reservoir array such that acoustic radiation is transmitted through each reservoir of the reservoir array. Such relative motion preferably results in displacement of the acoustic radiation generator in a direction along the columns, and does not result in displacement of the radiation generator in a direction other than along the columns. Thus, for example, when the reservoirs are provided in a rectilinear array having X rows and Y columns of reservoirs, wherein X and Y are each at least 2, an acoustic radiation generator may be used to interrogate each row of reservoirs in succession in a direction along the Y columns.

When a multiple-element acoustic radiation generator is used in combination with an array of reservoirs, it is preferred that the elements exhibit geometric correspondence to the array. For example, when a well plate is used, it is preferred that the spacing between wells corresponds with the spacing of the vibrational elements. In such instances, the elements of the acoustic generator may have the same spacing as the wells. To increase imaging resolution, the linear density of the elements may be a multiple, preferably a positive integer multiple of the linear density of the reservoirs. Similarly, the elements of may be sized according to the reservoirs. In some instances, a vibrational element may be of approximately the same size as a reservoir.

Similarly, it is preferred that the entire acoustic radiation generator be sized according to the reservoir array. For a typical well plate having a row length of about 72 mm, a phased acoustic array capable of generating an image field length of at least 72 mm may be used. To ensure that the phased acoustic array does not extend beyond the edges of the well plate, the phased acoustic array preferably has a length of less than about 85 mm. One such phased acoustic array having 84 elements on a 0.9 mm pitch and a normal operating frequency of 7.5 MHz may be obtained from Toray Techno of Shinga-ken Japan. Other acoustic radiation generators suitable for use with the invention are commercially available as well.

Thus, the invention also provides a method for acoustically assessing the contents of one or more reservoirs. The method involves providing a plurality of reservoirs, each reservoir adapted to contain a fluid, and positioning an acoustic radiation generator in acoustic coupling relationship to a selected reservoir. Once positioned, the acoustic radiation generator is actuated to generate acoustic radiation that is transmitted through at least a portion of the selected reservoir to an analyzer. The analyzer is then used to analyze acoustic radiation that has been transmitted through at least a portion of the selected reservoir, thereby assessing the contents of the selected reservoir. Optionally, the acoustic radiation generator may be repositioned to allow for the assessment of the contents of the remaining reservoirs as well. When the acoustic radiation generated has an image field of a size sufficient to interrogate a plurality of selected reservoirs at one time, the radiation is transmitted through an exterior surface of the selected reservoirs, and the selected reservoirs.

The inventive method may be carried out by using only certain components of the device described above or by employing the entire device. For example, when a transducer assembly is used as the acoustic generator, the acoustic radiation may be generated using electronic beam steering and/or electronic focusing. In addition, transmissive and reflective acoustic techniques may be used to assess the contents of the reservoir. Furthermore, when a rectilinear array is employed comprising rows and columns of reservoirs, the image field of the generated acoustic radiation is typically of a size sufficient to interrogate at least a row of reservoirs. Thus, the inventive method may be used to assess the contents of each reservoir or a row of reservoirs. Optionally, such assessment may be repeated for a different row of reservoirs. By repeating such assessment successively for neighboring rows of reservoirs, the contents of all reservoirs of the reservoir array may be assessed.

By analyzing the transmitted acoustic radiation, one may accurately determine the contents of the selected reservoirs. As discussed above, the assessment may involve determining the volume of fluid in the reservoir or determining a property of fluid in the reservoirs. The fluid properties that may be determined include, but are not limited to, viscosity, surface tension, acoustic impedance, density, solid content, impurity content, acoustic attenuation, and pathogen content. In some instances, the assessment may involve measuring the travel time of acoustic radiation through the reservoirs. In addition, or in the alternative, the assessment may involve determining the difference of acoustic radiation before and after transmission through the reservoirs.

Those of ordinary skill in the art will appreciate that conventional or modified sonar techniques may be employed. For example, reflected acoustic radiation may be converted into electrical energy for analysis. The analysis may be used, for example, to reveal whether the reservoir contains any fluid at all. If fluid is present in the reservoir, the location and the orientation of the free fluid surface within the reservoir may be determined, as well as the overall volume of the fluid. Characteristics of the reflected acoustic radiation may be analyzed in order to assess the spatial relationship between the acoustic radiation generator and the fluid surface, the spatial relationship between a solid surface of the reservoir and the fluid surface.

Depending on the type of assessment to be carried out, various techniques known in the art may be adapted for use in the present invention. Generally, interfacial energy measurements are routinely carried out using contact-angle measurements. The present invention may be adapted to perform such contact-angle measurements. In addition, a number of other acoustic assessment techniques are known in the art. For example, U.S. Pat. No. 4,391,129 to Trinh describes a system for monitoring the physical characteristics of fluids. A physical characteristic may be determined from acoustic assessment of the interfacial tension of fluids to a high degree of accuracy. U.S. Pat. No. 4,558,589 to Hemmes describes an ultrasonic blood-coagulation monitor. U.S. Pat. No. 5,056,357 to Dymling et al. describes acoustic methods for measuring properties in fluids through Doppler shifts. Other acoustic assessment techniques that may be adapted for use in the present invention are described, for example, in U.S. Pat. Nos. 4,901,245; 5,255,564; 5,410,518; 5,471,872; 5,533,402; 5,594,165; 5,623,095; 5,739,432; 5,767,407; 5,793,705; 5,804,698; 6,119,510; 6,227,040; and 6,298,726.

In addition or in the alternative, the invention may also employ directed and/or focused acoustic radiation to enhance reservoir content assessment. For example, acoustic radiation may be used to perturb the surface of a fluid as well as to monitor the perturbation. Such perturbation techniques are well suited for use in determining the surface tension and viscosity of fluids, or the effect. Such techniques are generally sufficiently accurate and precise for measuring the effect small amounts of additives (e.g., pharmaceutical composition, biomolecular samples, etc.) have on the surface tension or viscosity of the fluids. Notably, such perturbation techniques should complement ordinary acoustic impedance measurement In some embodiments, the invention provides a method for monitoring a change in the amount and/or concentration of organisms in a culture fluid. That is, acoustic radiation is used to monitor changes in the amount and/or concentration of the organism in the reservoirs. For example, a bacterial culture may be placed in the reservoirs and subjected to a temperature change selected to facilitate an increase or decrease in the amount and/or concentration of the bacteria in the reservoirs. Acoustic radiation may be used to monitor bacterial growth in the reservoirs. Such monitoring techniques may also be applied to other biological or chemical systems such as those constructed for PCR, wherein any moiety, e.g., a nucleotidic biomolecule, is replicated. It should be noted, however, that the invention may be used to monitor the content of any organism or moiety, irrespective of whether the organism is a pathogen. Such monitoring techniques, as applied to pathogenic fluids, are described in U.S. patent application Ser. No. 10/199,907 for "Acoustic Radiation for Ejecting and Monitoring Pathogenic Fluids," filed Jul. 18, 2002, inventors Mutz and Ellson (assigned to Picoliter Inc., Sunnyvale, Calif.).

As discussed above, the reservoirs may be constructed to reduce the amount of movement and time needed to align the acoustic radiation generator with each reservoir or reservoir well during operation. As a general matter of convenience and efficiency, it is desirable to analyze an entire library of different moieties in a relatively short amount of time, e.g., about one minute.

Thus, the inventive method typically allows for the analysis of the contents of the reservoirs at a rate of at least about 96 reservoirs per minute. Faster analysis rates of at least about 384, 1536, and 3456 reservoirs per minute are achievable with present day technology as well. Thus, the invention can be operated to analyze the contents of each well of most (if not all) well plates that are currently commercially available. Generally, it is desirable to carry out acoustic assessment of the reservoirs at a rate of at least about 5 reservoirs per second. Preferably, the assessment is carried out at a rate of at least about 10 reservoirs per second. More preferably, the assessment is carried out at a rate of at least about 25 reservoirs per second. It is envisioned that optimal implementation of the inventive method should yield a reservoir assessment rate of at least about 10,000 reservoirs per minute. Thus, depending on the assessment rate and the number of reservoirs, the contents of all reservoirs may be assessed in no more than 5 minutes, preferably in one minute or less.

Acoustic assessment as described above may be employed to improve fluid dispensing from each of a plurality of reservoirs adapted to contain a fluid. Thus, the invention may be used in conjunction with a number of known techniques for dispensing fluids involving contact-based fluid dispensing, e.g., pin spotting, pipetting, and inkjet printing, or non-contact based fluid dispensing, e.g., acoustic ejection. Since acoustic ejection provides a number of advantages over other fluid dispensing technologies, the device may also include an ejector and a means for positioning the ejector to eject fluid from any of the reservoirs. Typically, the acoustic ejector employs focused acoustic radiation to effect fluid ejection and the means for positioning the ejector is adapted to position the ejector in acoustic coupling relationship to each of the reservoirs. As described in U.S. Patent Application Publication No. 20020037579 to Ellson et al., an acoustic ejector may comprise an acoustic radiation generator for generating acoustic radiation and a focusing means for focusing the acoustic radiation generated at a focal point within and sufficiently near the fluid surface in each of a plurality of reservoirs to result in the ejection of droplets therefrom. Thus, the invention also provides a device that can carry out both acoustic ejection and assessment.

In the present invention, any of a variety of focusing means may be employed to focus acoustic radiation so as to eject droplets from a reservoir. For example, one or more curved surfaces may be used to direct acoustic radiation to a focal point near a fluid surface. One such technique is described in U.S. Pat. No. 4,308,547 to Lovelady et al. Focusing means with a curved surface have been incorporated into the construction of commercially available acoustic transducers such as those manufactured by Panametrics Inc. (Waltham, Mass.). In addition, Fresnel lenses are known in the art for directing acoustic energy at a predetermined focal distance from an object plane. See, e.g., U.S. Pat. No. 5,041,849 to Quate et al. Fresnel lenses may have a radial phase profile that diffracts a substantial portion of acoustic energy into a predetermined diffraction order at diffraction angles that vary radially with respect to the lens. The diffraction angles should be selected to focus the acoustic energy within the diffraction order on a desired object plane. Optimally, the device is adapted to eject fluid from a reservoir according to the results of acoustic analysis performed by the analyzer.

A single ejector is preferred, although the inventive device may include a plurality of ejectors. When a single ejector is employed, the positioning means should allow for the ejector to move from one reservoir to another quickly and in a controlled manner, thereby allowing fast and controlled scanning of the reservoirs to effect droplet ejection therefrom. In some instances, the same acoustic radiation generator may be used to effect both acoustic assessment and ejection. Acoustic assessment and ejection may also be carried out using separate acoustic generators.

The means for positioning the ejector may be adapted to provide relative motion between the ejector and reservoirs according to the reservoir content assessment made by the analyzer. In such a case, the ejector may be maintained at a constant distance from the acoustic radiation generator. Accordingly, when rows of reservoirs are provided, relative motion between the acoustic radiation generator and the reservoirs may result in displacement of the acoustic radiation generator in a direction along the rows. Alternatively, the means for positioning the ejector is adapted to provide relative motion between the ejector and reservoir array independently from the reservoir content assessment made by the analyzer. In any case, when a rectilinear array of reservoirs is provided, the ejector may be movable in a row-wise direction and/or in a direction perpendicular to both the rows and columns.

When an ejector is employed, the invention may be used to eject fluid from the reservoirs onto a substrate. For example, it is described in U.S. Patent Application Publication No. 20020037579 to Ellson et al. that such acoustic ejection technology may be used to form biomolecular arrays. Similarly, acoustic ejection technology may be employed to format a plurality of fluids, e.g., to transfer fluids from odd-sized bulk containers to wells of a standardized well plate or to transfer fluids from one well plate to another. One skilled in the art will recognize that such acoustic ejection technologies may be adapted for a variety of applications. In such applications, a means for positioning the substrate may be employed to provide relative motion between the substrate and the reservoirs.

As discussed above, relative motion may be classified as pulse or continuous. In order to ensure optimal performance. Either type of design may be employed for providing relative motion between the ejector and the reservoirs for fluid ejection. Similarly, either type of motion may result in relative displacement between the acoustic generator and the reservoirs, as well as relative displacement between the substrate and the reservoirs. Thus, the above-described positioning technology for the acoustic generator may be used to move a separate acoustic analyzer and/or acoustic ejector.

In some instances, high-speed robotic systems may be employed to handle the reservoirs, the acoustic generator and/or the ejector. In some instances, a decision may be made as to whether and/or how to dispense fluid from the reservoir depending on the results of acoustic analysis. For example, when an acoustic ejector is employed, operating parameters relating to the ejector may be determined by using the data from the above-described assessment relating to reservoir volume or fluid property data, as well as geometric data associated with the reservoir. In addition, the data may show the need to reposition the ejector so as to reposition the acoustic radiation generator with respect to the fluid surface, in order to ensure that the focal point of the ejection acoustic wave is near the fluid surface, where desired. For example, if analysis reveals that the acoustic radiation generator is positioned such that the ejection acoustic wave cannot be focused near the fluid surface, the acoustic radiation generator is repositioned using vertical, horizontal, and/or rotational movement to allow appropriate focusing of the ejection acoustic wave.

In some embodiments, the inventive device also includes a means for removing fluid acoustic coupling medium from the exterior surface of one or more reservoirs where the acoustic radiation generator is not acoustically coupled thereto. Typically, such means employs vacuum technology. For example, suction may be applied to either pull the coupling medium into a collection vessel or to accelerate evaporation of the coupling medium. In addition, the means for removing the fluid acoustic coupling medium employs a blade that conforms to the exterior surface of one or more reservoirs. Such a blade may be comprised of an elastomeric material and generally operates on the same principle employed when a windshield wiper or a squeegee is slid across a surface to remove water therefrom. Furthermore, the coupling medium may be removed through the use of an absorbent material through wiping or blotting action. Similarly, vacuum technology may be used to remove fluid acoustic coupling medium from the reservoir surfaces. One skilled in the art will recognize that other fluid removal technologies may be used in conjunction with the invention as well. Optionally, when a plurality of reservoirs is employed, fluid coupling medium removal may be simultaneously carried out with acoustic assessment, as long as the removal of acoustic coupling does not interfere with acoustic assessment. That is, as long as sufficient acoustic coupling medium is present for assessment, any excess acoustic coupling fluid present on a surface may be removed simultaneously with acoustic assessment occurring elsewhere.

It should be noted that acoustic coupling medium removal represents an important aspect of the invention because the acoustic coupling medium may represent a source of contamination. For example, DMSO, as discussed above, is highly hygroscopic and tends to absorb and become diluted by any ambient water with which it comes into contact. Should water or an aqueous fluid be used as the acoustic coupling medium when one or more reservoirs contain DMSO, it is desirable to limit the exposure of reservoirs to the acoustic coupling medium. Thus, in most instances, the acoustic coupling medium should be removed soon after it is needed. In particular, when high-speed handling systems are employed, any fluid coupling medium remaining on the exterior surface of the reservoirs may experience the forces associated with large accelerations and decelerations. As a result, such remaining fluid coupling medium may be uncontrollably flung from the surface. If the fluid coupling medium lands in a reservoir, the content contained in the reservoir will be changed.

The invention may employ or provide certain additional performance-enhancing functionalities. Thus, the invention may employ a storage means comprising rewritable and/or permanent data storage media for storing the results of acoustic analysis performed by the analyzer. Such data may be used immediately, e.g., to enhance fluid ejection, and/or stored for future use. In some instance, the invention may be used to determine the location and/or geometries associated of one or more reservoirs within a reservoir unit.

In addition, for fluids that exhibit temperature-dependent properties, a temperature measurement means known in art, such as thermocouples, may be used in conjunction with such analyses. Temperature controlling means may be also employed to improve the accuracy of measurement and may be employed regardless of whether the device includes a fluid dispensing functionality. In the case of aqueous fluids, the temperature controlling means should have the capacity to maintain the reservoirs at a temperature above about 0° C. In addition, the temperature controlling means may be adapted to lower the temperature in the reservoirs. Such temperature lowering may be required because repeated application of acoustic energy to a reservoir of fluid may result in heating of the fluid. Such heating can result in unwanted changes in fluid properties such as viscosity, surface tension, and density. Design and construction of such temperature controlling means are known to one of ordinary skill in the art and may comprise, e.g., components such a heating element, a cooling element, or a combination thereof.

For many biomolecular applications, reservoirs of fluids are stored frozen and thawed for use. During use, it is generally desired that the fluid containing the biomolecule be kept at a constant temperature, with deviations of no more than about 1° C. or 2° C. therefrom. In addition, for a biomolecular fluid that is particularly heat sensitive, it is preferred that the fluid be kept at a temperature that does not exceed about 10° C. above the melting point of the fluid, preferably at a temperature that does not exceed about 5° C. above the melting point of the fluid. Thus, for example, when the biomolecule-containing fluid is aqueous, it may be optimal to keep the fluid at about 4° C. during ejection.

Moreover, the invention may be adapted to assess and/or dispense fluids of virtually any type and amount desired. The fluid may be aqueous and/or nonaqueous. Examples of fluids include, but are not limited to, aqueous fluids including water per se and water-solvated ionic and non-ionic solutions, organic solvents, lipidic liquids, suspensions of immiscible fluids, and suspensions or slurries of solids in liquids. Because the invention is readily adapted for use with high temperatures, fluids such as liquid metals, ceramic materials, and glasses may be used; see, e.g., U.S. Patent Application Publication Nos. 2002007375 and 2002155231 to Ellson et al. Furthermore, because of the precision that is possible using the inventive technology, the invention may be used to eject droplets from a reservoir adapted to contain no more than about 100 nL of fluid, preferably no more than 10 nL of fluid. In certain cases, the ejector may be adapted to eject a droplet from a reservoir adapted to contain about 1 to about 100 nL of fluid. This is particularly useful when the fluid to be ejected contains rare or expensive biomolecules, wherein it may be desirable to eject droplets having a volume of about 1 picoliter or less, e.g., having a volume in the range of about 0.025 pL to about 1 pL.

It should be noted that there are a number of different ways to combine acoustic assessment with fluid dispensing, depending on the intended purpose of the combination. As discussed above, fluid may be dispensed from a reservoir after the contents of the reservoir are acoustically assessed. This allows an operator to fine tune the dispensing according to the condition of the contents of the reservoir. In addition, fluid may be dispensed from a reservoir before the contents of the reservoir are acoustically assessed. In such a case, acoustic assessment may serve to confirm the quality of fluid dispensation as well as to ensure that the dispensing process does not unexpectedly alter the contents of the reservoir. For example, by assessing the volume of fluid remaining in a reservoir after a fluid has been dispensed from the reservoir, an operator may determine the quantity of fluid actually removed from the reservoir. In some instances, acoustic assessment and fluid dispensation may occur simultaneously.

Thus, another embodiment of the invention relates to a method for dispensing fluid from one or more reservoirs. Once an acoustic radiation generator is positioned, in acoustic coupling relation to a reservoir selected from a plurality of reservoirs, acoustic radiation generated by the acoustic radiation generator may be transmitted through at least a portion of the selected reservoir. The acoustic radiation is then analyzed in order to assess the contents of the reservoir, and fluid is dispensed from the selected reservoir according to the assessment. Typically, the fluid is dispensed through acoustic ejection, though the inventive method may employ contact-based fluid dispensing either as an alternative to or as a supplement to noncontact-based fluid dispensing. Optionally, the above process may be repeated for additional reservoirs.

It should be noted that there are a number of different ways to combine acoustic assessment with fluid dispensing, depending on the intended purpose of the combination. As discussed above, fluid may be dispensed from a reservoir after the contents of the reservoir are acoustically assessed. This allows an operator to fine tune the dispensing according to the condition of the contents of the reservoir. In addition, fluid may be dispensed from a reservoir before the contents of the reservoir are acoustically assessed. In such a case, acoustic assessment may serve to confirm the quality of fluid dispensation as well as to ensure that the dispensing process does not unexpectedly alter the contents of the reservoir. For example, by assessing the volume of fluid remaining in a reservoir after a fluid has been dispensed from the reservoir, an operator may determine the quantity of fluid actually removed from the reservoir. In some instances, acoustic assessment and fluid dispensation may occur simultaneously.

FIG. 1 illustrates a preferred embodiment of the inventive device in simplified cross-sectional view. In this embodiment, the inventive device allows for acoustic assessment of the contents of a plurality of reservoirs as well as acoustic ejection of fluid droplets from the reservoirs. The inventive device is shown in operation to form a biomolecular array bound to a substrate. As with all figures referenced herein, in which like parts are referenced by like numerals, FIG. 1 is not to scale, and certain dimensions may be exaggerated for clarity of presentation. The device 11 includes a plurality of reservoirs, i.e., at least two reservoirs, with a first reservoir indicated at 13 and a second reservoir indicated at 15. Each is adapted to contain a fluid having a fluid surface. As shown, the first reservoir 13 contains a first fluid 14 and the second reservoir 15 contains a second fluid 16. Fluids 14 and 16 each have a fluid surface respectively indicated at 14S and 16S. Fluids 14 and 16 may the same or different. As shown, the reservoirs are of substantially identical construction so as to be substantially acoustically indistinguishable, but identical construction is not a requirement. The reservoirs are shown as separate removable components but may, as discussed above, be fixed within a plate or other substrate. For example, the plurality of reservoirs may comprise individual wells in a well plate, optimally although not necessarily arranged in an array. Each of the reservoirs 13 and 15 is preferably axially symmetric as shown, having vertical walls 13W and 15W extending upward from circular reservoir bases 13B and 15B and terminating at openings 13O and 15O, respectively, although other reservoir shapes may be used. The material and thickness of each reservoir base should be such that acoustic radiation may be transmitted therethrough and into the fluid contained within the reservoirs.

The device also includes an acoustic ejector 33 comprised of an acoustic radiation generator 35 for generating acoustic radiation and a focusing means 37 for focusing the acoustic radiation at a focal point within the fluid from which a droplet is to be ejected, near the fluid surface. The acoustic radiation generator contains a transducer 36, e.g., a piezoelectric element, commonly shared by an analyzer. As shown, a combination unit 38 is provided that both serves as a controller and a component of an analyzer. Operating as a controller, the combination unit 38 provides the piezoelectric element 36 with electrical energy that is converted into mechanical and acoustic energy. Operating as a component of an analyzer, the combination unit receives and analyzes electrical signals from the transducer. The electrical signals are produced as a result of the absorption and conversion of mechanical and acoustic energy by the transducer.

As shown in FIG. 1, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15, and thus to fluids 14 and 16, respectively. The acoustic radiation generator 35 and the focusing means 37 may function as a single unit controlled by a single controller, or they may be independently controlled, depending on the desired performance of the device. Typically, single ejector designs are preferred over multiple ejector designs because accuracy of droplet placement and consistency in droplet size and velocity are more easily achieved with a single ejector.

There are also a number of ways to acoustically couple the ejector 33 to each individual reservoir and thus to the fluid therein. One such approach is through direct contact as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. However, this approach for acoustically coupling the focusing means to a fluid is undesirable when the ejector is used to eject different fluids in a plurality of containers or reservoirs, as repeated cleaning of the focusing means would be required in order to avoid cross-contamination. The cleaning process would necessarily lengthen the transition time between each droplet ejection event. In addition, in such a method, fluid would adhere to the ejector as it is removed from each container, wasting material that may be costly or rare.

Thus, a preferred approach would be to acoustically couple the ejector to the reservoirs and reservoir fluids without contacting any portion of the ejector, e.g., the focusing means, with any of the fluids to be ejected. To this end, the present invention provides an ejector positioning means for positioning the ejector in controlled and repeatable acoustic coupling with each of the fluids in the reservoirs to eject droplets therefrom without submerging the ejector therein. This typically involves direct or indirect contact between the ejector and the external surface of each reservoir. When direct contact is used in order to acoustically couple the ejector to each reservoir, it is preferred that the direct contact is wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs having a specially formed inverse surface.

Optimally, acoustic coupling is achieved between the ejector and each of the reservoirs through indirect contact, as illustrated in FIG. 1A. In this figure, an acoustic coupling medium 25 is placed between the ejector 33 and the base 13B of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is important to ensure that the fluid medium is substantially free of material having different acoustic properties than the fluid medium itself. Furthermore, it is preferred that the acoustic coupling medium is comprised of a material having acoustic properties that facilitate the transmission of acoustic radiation without significant attenuation in acoustic pressure and intensity. Also, the acoustic impedance of the coupling medium should facilitate the transfer of energy from the coupling medium into the container. As shown, the first reservoir 13 is acoustically coupled to the acoustic focusing means 37, such that an acoustic wave is generated by the acoustic radiation generator and directed by the focusing means 37 into the acoustic coupling medium 25, which then transmits the acoustic radiation into the reservoir 13.

In operation, reservoirs 13 and 15 are each filled with first and second fluids 14 and 16, respectively, as shown in FIG. 1. The acoustic ejector 33 is positionable by means of ejector positioning means 61, shown below reservoir 13, in order to achieve acoustic coupling between the ejector and the reservoir through acoustic coupling medium 25. Once the ejector, the reservoir, and the substrate are in proper alignment, the acoustic radiation generator 35 is activated to produce acoustic radiation that is directed toward a free fluid surface 14S of the first reservoir. The acoustic radiation will then travel in a generally upward direction toward the free fluid surface 14S. The acoustic radiation will be reflected under different circumstances. Typically, reflection will occur when there is a change in the acoustic property of the medium through which the acoustic radiation is transmitted. It has been observed that a portion of the acoustic radiation traveling upward will be reflected from by the reservoir bases 13B and 15B as well as the free surfaces 14S and 16S of the fluids contained in the reservoirs 13 and 15.

As discussed above, acoustic radiation may be employed for use as an analytical tool as well as to eject droplets from a reservoir. In an analytical mode, the acoustic radiation generator is typically activated so as to generate low energy acoustic radiation that is insufficiently energetic to eject a droplet from the fluid surface. This is typically done by using an extremely short pulse (on the order of tens of nanoseconds) relative to that required for droplet ejection (on the order of microseconds). By determining the time it takes for the acoustic radiation to be reflected by the fluid surface back to the acoustic radiation generator, and then correlating that time with the speed of sound in the fluid, the distance—and thus the fluid height—may be calculated. Of course, care must be taken in order to ensure that acoustic radiation reflected by the interface between the reservoir base and the fluid is accounted for and discounted so that acoustic assessment is based on the travel time of the acoustic radiation within the fluid only.

Thus, the present invention represents a significant improvement over known technologies relating to the acoustic assessment of the contents of a plurality of reservoirs. As discussed above, acoustic assessment of the contents liquid reservoirs typically involves placing a sensor in direct contact with the liquid. This means that the sensor must be cleaned between each use to avoid cross-contamination of the contents of the reservoirs. In contrast, the invention allows for assessment of the contents of a plurality of containers without direct contact with the contents of the containers.

While other non-contact acoustic systems are known in the art, such systems provide only an indirect and approximate assessment of the contents of a reservoir. For example, the acoustic system described in U.S. Pat. No. 5,880,364 to Dam employs a technique in which the acoustic radiation is transmitted from a sensor through an air-containing portion of the container and then reflected from the air-liquid interface of the container back to the sensor. The round trip transit time is used to determine the volume of the air-containing portion of the container. The volume of liquid in the container is determined by subtracting the volume of the container not occupied by the liquid from the volume of the entire container. One drawback of this technique is that it cannot provide an accurate assessment of the liquid volume in a container when the volume of the container is not precisely known. This is particularly problematic when small reservoirs such as those typically used in combinatorial techniques are employed. The dimensional variability for such containers is relatively large when considered in view of the small volume of the reservoirs. Furthermore, the technique cannot be employed when the volume of the container is completely unknown or alterable. Finally, since acoustic radiation never penetrates the liquid, the reflected radiation can at best only provide information relating to the surface of the liquid, not information relating to the bulk of the liquid.

In contrast, because the invention involves the transmission of acoustic radiation through the portion of each reservoir adapted to contain a fluid, the transmitted acoustic radiation may provide information relating to the volume as well as the properties of the fluids in the reservoir. For example, the invention provides a plurality of reservoirs, wherein a portion of each reservoir is adapted to contain a fluid. A fluid contained in a reservoir must ordinarily contact a solid surface of the reservoir. When the invention is employed in a reflective mode, some of the generated acoustic radiation may be reflected by interface between the fluid and the solid surface, while the remainder is transmitted through a fluid contained in the reservoir. The transmitted radiation is then reflected by another surface, e.g., a free surface, of the fluid contained in the reservoir. By determining the difference in round-trip transit time between the two portions, the volume of the fluid in the reservoir may be accurately determined. In addition, transmission of acoustic radiation through the fluid allows characteristics of the acoustic radiation to be altered by fluid. Thus, information relating to a property of the fluid may be deduced by analyzing a characteristic of the transmitted acoustic radiation.

In addition, air, like other gases, exhibits low acoustic impedance, and acoustic radiation tends to attenuate more in gaseous materials than in liquid or solid materials. For example, the attenuation at 1 MHz for air is approximately 10 dB/cm while that of water is 0.002 dB/cm. Since the acoustic system described in U.S. Pat. No. 5,880,364 to Dam requires acoustic radiation to travel through air, this system requires much more energy to operate. Thus, the present invention represents a more energy efficient technology that may be employed to provide more accurate and detailed assessment of the contents of a plurality of fluid reservoirs. Some of this additional accuracy can be achieved by using higher frequency acoustic waves (and hence shorter wavelengths) as these acoustic waves can be transmitted effectively through liquids yet would be very rapidly attenuated in air.

In order to form a biomolecular array on a substrate using the inventive device, substrate 53 is positioned above and in proximity to the first reservoir 13 such that one surface of the substrate, shown in FIG. 1 as underside surface 51, faces the reservoir and is substantially parallel to the surface 14S of the fluid 14 therein. Once the ejector, the reservoir, and the substrate are in proper alignment, the acoustic radiation generator 35 is activated to produce acoustic radiation that is directed by the focusing means 37 to a focal point 14P near the fluid surface 14S of the first reservoir. That is, an ejection acoustic wave having a focal point near the fluid surface is generated in order to eject at least one droplet of the fluid.

The optimum intensity and directionality of the ejection acoustic wave is determined using the aforementioned analysis, optionally in combination with additional data. That is, any of the conventional or modified sonar techniques discussed above may be employed. The "optimum" intensity and directionality are generally selected to produce droplets of consistent size and velocity. For example, the desired intensity and directionality of the ejection acoustic wave may be determined by using the data from the above-described assessment relating to reservoir volume or fluid property data, as well as geometric data associated with the reservoir. In addition, the data may show the need to reposition the ejector so as to reposition the acoustic radiation generator with respect to the fluid surface, in order to ensure that the focal point of the ejection acoustic wave is near the fluid surface, where desired. For example, if analysis reveals that the acoustic radiation generator is positioned such that the ejection acoustic wave cannot be focused near the fluid surface, the acoustic radiation generator is repositioned using vertical, horizontal, and/or rotational movement to allow appropriate focusing of the ejection acoustic wave.

As a result, droplet 14D is ejected from the fluid surface 14S onto a designated site on the underside surface 51 of the substrate. The ejected droplet may be retained on the substrate surface by solidifying thereon after contact; in such an embodiment, it may be necessary to maintain the substrate at a low temperature, i.e., a temperature that results in droplet solidification after contact. Alternatively, or in addition, a molecular moiety within the droplet attaches to the substrate surface after contract, through adsorption, physical immobilization, or covalent binding.

Figure 1B:
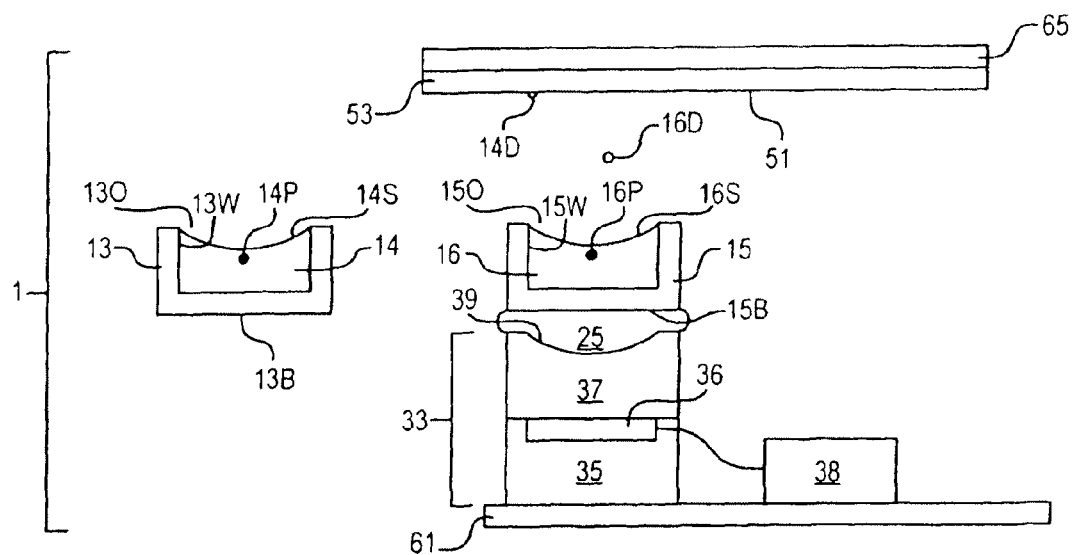

Then, as shown in FIG. 1B, a substrate positioning means 65 repositions the substrate 53 over reservoir 15 in order to receive a droplet therefrom at a second designated site. FIG. 1B also shows that the ejector 33 has been repositioned by the ejector positioning means 61 below reservoir 15 and in acoustically coupled relationship thereto by virtue of acoustic coupling medium 25. Once properly aligned, the acoustic radiation generator 35 of ejector 33 is activated to produce low energy acoustic radiation to assess the contents of the reservoir 15 and to determine whether and/or how to eject fluid from the reservoir. Historical droplet ejection data associated with the ejection sequence may be employed as well. Again, there may be a need to reposition the ejector so as to reposition the acoustic radiation generator with respect to the fluid surface, in order to ensure that the focal point of the ejection acoustic wave is near the fluid surface, where desired. Should the results of the assessment indicate that fluid may be dispensed from the reservoir, focusing means 37 is employed to direct higher energy acoustic radiation to a focal point 16P within fluid 16 near the fluid surface 16S, thereby ejecting droplet 16D onto the substrate 53.

It will be appreciated that various components of the device may require individual control or synchronization to form an array on a substrate. For example, the ejector positioning means may be adapted to eject droplets from each reservoir in a predetermined sequence associated with an array to be prepared on a substrate surface. Similarly, the substrate positioning means for positioning the substrate surface with respect to the ejector may be adapted to position the substrate surface to receive droplets in a pattern or array thereon. Either or both positioning means, i.e., the ejector positioning means and the substrate positioning means, may be constructed from, for example, motors, levers, pulleys, gears, a combination thereof, or other electromechanical or mechanical means known to one of ordinary skill in the art. It is preferable to ensure that there is a correspondence between the movement of the substrate, the movement of the ejector, and the activation of the ejector to ensure proper array formation.

Accordingly, the invention relates to the assessment of the contents of a plurality of reservoirs as well as to dispensing a plurality of fluids from reservoirs, e.g., in order to form a pattern or an array, on the substrate surface 51. However, there are a number of different ways in which content assessment and fluid dispensing may relate to each other. That is, a number of different sequences may be employed for assessing the contents of the reservoirs and for dispensing fluids therefrom. In some instances, the contents of a plurality of reservoirs may be assessed before fluid is dispensed from any of the reservoirs. In other instances, the contents of each reservoir may be assessed immediately before fluid is dispensed therefrom. The sequence used typically depends on the particular fluid-dispensing technique employed as well as the intended purpose of the sequence.

Figure 2:
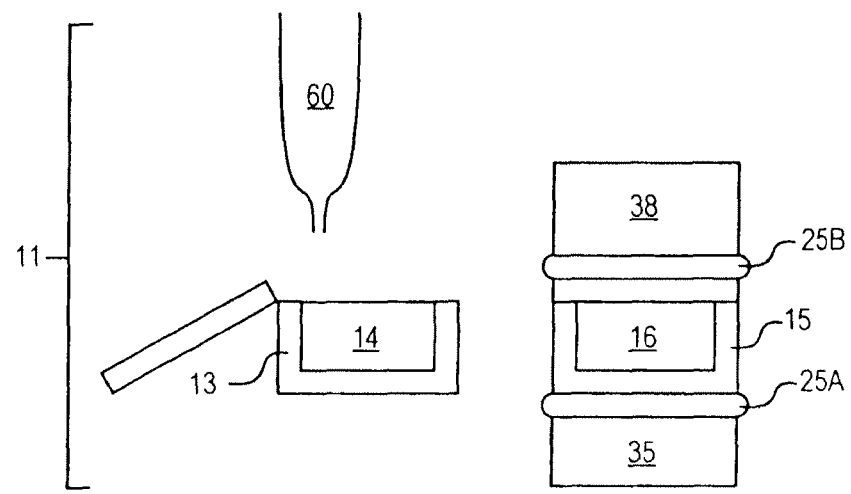
FIG. 2 schematically illustrates in simplified cross-sectional view an embodiment of the inventive device designed to permit acoustical assessment of the contents of a plurality of reservoirs in transmissive mode.

FIG. 2 illustrates an example of the inventive device that provides for assessment of the contents of a plurality of reservoirs in transmissive mode rather than in reflective mode. Considerations for the design and construction of this device are similar to those discussed above. Thus, the device 11 includes a first reservoir 13 and a second reservoir 15, each adapted to contain a fluid indicated at 14 and 16, respectively, and each of substantially identical construction. The first reservoir 13 is depicted in an open state, while the second reservoir is depicted in a sealed state. An acoustic radiation generator 35 is positioned below the reservoirs, and analyzer 38 is positioned in opposing relationship with the acoustic radiation generator 35 above the reservoirs.

Figure 3A:
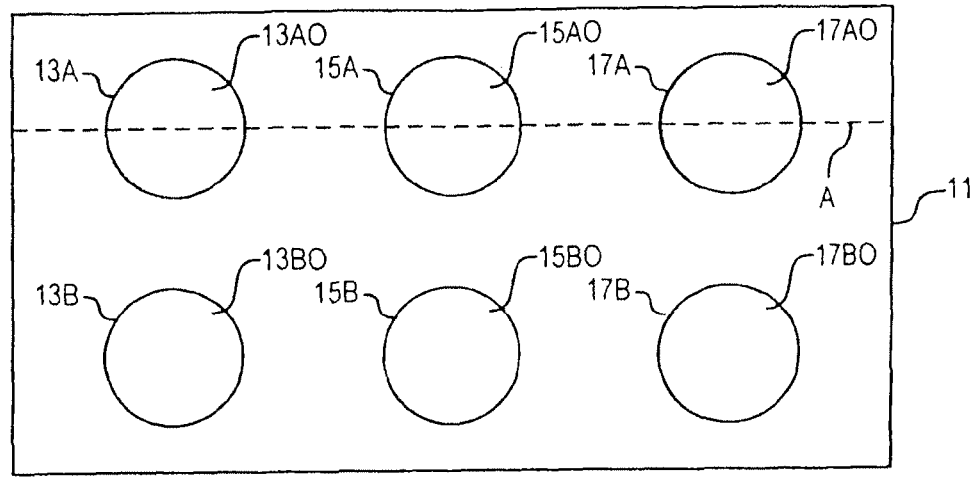
FIGS. 3A-3C, collectively referred to as FIG. 3, schematically illustrate a rectilinear array of reservoirs in the form of a well plate having three rows and two columns of wells.
Figure 3B:
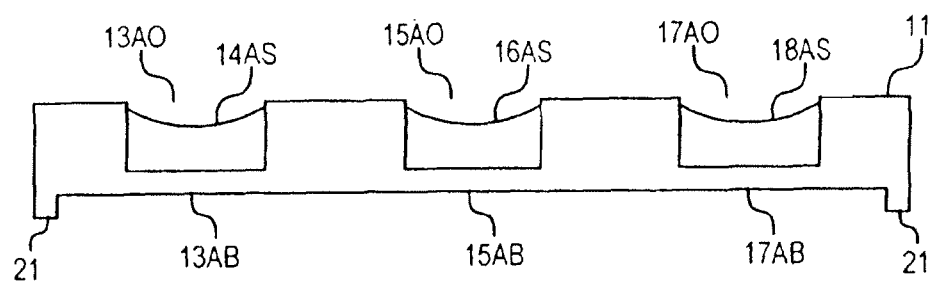
Figure 3C:
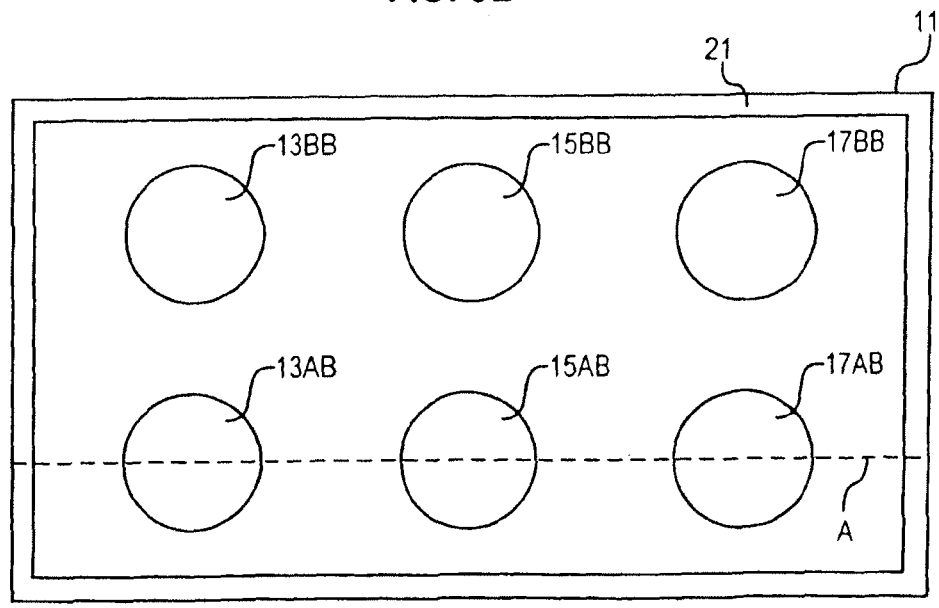

In operation, the contents of each of the reservoirs are acoustically evaluated before pipette 60 is employed to dispense fluid therefrom. As shown, the contents 14 of the first reservoir 13 have already been acoustically assessed. As the assessment has revealed that the first reservoir 13 contains at least a minimum acceptable level of fluid 14, the first reservoir 13 is open and ready for fluid to be dispensed therefrom via pipette 60. The contents 16 of the second reservoir 15 are undergoing acoustic assessment, as depicted by FIG. 2, as the second reservoir 15 is interposed between the acoustic radiation generator 35 and the analyzer 38. The acoustic radiation generator 35 and the analyzer 38 are acoustically coupled to the second reservoir via coupling media 25A and 25B, respectively. Once the acoustic radiation generator 35, the second reservoir 15, and the analyzer 38 are in proper alignment, the acoustic radiation generator 35 is activated to produce acoustic radiation that is transmitted through the reservoir 15 and its contents 16 toward the analyzer 38. The received acoustic radiation is analyzed by an analyzer 38 as described above FIG. 3 schematically illustrates an exemplary rectilinear array of reservoirs that may be used with the invention. The reservoir array is provided in the form of a well plate 11 having three rows and two columns of wells. As depicted in FIGS. 3A and 3C, wells of the first, second, and third rows of wells are indicated at 13A and 13B, 15A and 15B, and 17A and 17B, respectively. Each is adapted to contain a fluid having a fluid surface. As depicted in FIG. 3B, for example, reservoirs 13A, 15A, and 17A contain fluids 14A, 16A, and 18A, respectively. The fluid surfaces for each fluid are indicated at 14AS, 16AS, and 18AS. As shown, the reservoirs are of substantially identical construction so as to be substantially acoustically indistinguishable, but identical construction is not a requirement. Each of the depicted reservoirs is axially symmetric, having vertical walls extending upward from circular reservoir bases indicated at 13AB, 13BB, 15AB, 15BB, 17AB, and 17BB, and terminating at corresponding openings indicated at 13AO, 13BO, 15AO, 15BO, 17AO, and 17BO. The bases of the reservoirs form a common exterior lower surface 19 that is substantially planar. Although a full well plate skirt (not shown) may be employed that extends from all edges of the lower well plate surface, as depicted, partial well plate skirt 21 extends downwardly from the longer opposing edges of the lower surface 19. The material and thickness of the reservoir bases are such that acoustic radiation may be transmitted therethrough and into the fluid contained within the reservoirs.

Figure 4:
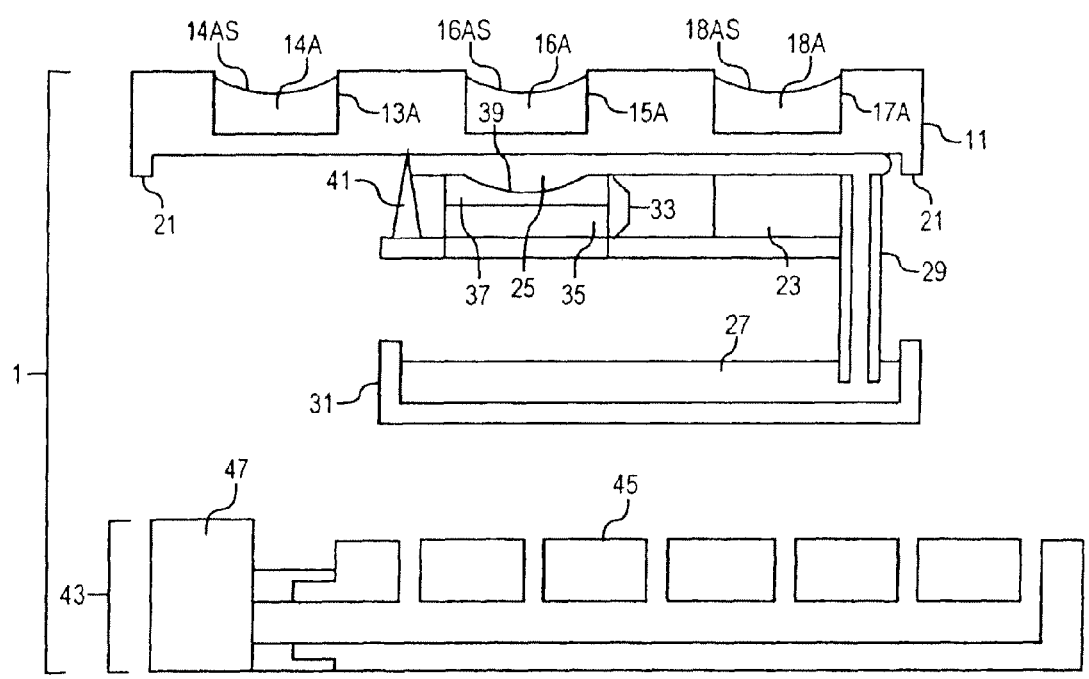
FIG. 4 schematically illustrates in side view a preferred embodiment of the inventive device using the well plate depicted in FIG. 3.

FIG. 4 schematically illustrates in side view a preferred embodiment of the inventive device using the well plate depicted in FIG. 3. The exemplary device 1 depicted in FIG.

4 allows for acoustic assessment of the contents of a plurality of reservoirs and acoustic ejection of fluid droplets from the reservoirs in order to attach biomolecules to a substrate surface. In addition to the well plate 11, the device also includes an acoustic generator in the form of a transducer assembly. More particularly, the transducer assembly is a phased acoustic array 23 that serves both as the acoustic radiation generator and the analyzer. As shown in FIG. 6, the phased acoustic array 23 has a generally rectangular surface from which acoustic radiation is emitted. Also as depicted, the length of the rectangular surface is aligned with the rows of wells. To ensure proper acoustic coupling between the well plate 11 and the phased acoustic array 23 (as discussed below), it is preferred that the phased acoustic array 23 exceeds the length of the rows of wells in the well plate but is no greater than the distance between the sections of the skirt 21 along the columnwise edges of the well plate 11. That is, the length of the phased acoustic array is approximately that of the width of the well plate (or length if the well plate has longer rows than columns).

The phased acoustic array 23 as depicted is acoustically coupled to the well plate 11 without contacting any of the fluids within the wells of the well plate 11. This typically involves either direct or indirect contact between the ejector and the exterior lower surface 19 of the well plate 11. When direct contact is used in order to acoustically couple the phased acoustic array 23 to the well plate 11, it is preferred that the direct contact is wholly conformal to ensure efficient acoustic energy transfer. That is, the surface of the phased acoustic array from which acoustic radiation is emitted and the lower surface of the well plate should have corresponding surfaces adapted for mating contact. Without conformal contact, efficiency and accuracy of acoustic energy transfer may be compromised.

As depicted in FIG. 4, acoustic coupling is achieved between the phased acoustic array 23 and the well plate 11 through indirect contact to enhance transfer of acoustic radiation. In this figure, a fluid acoustic coupling medium 25 is placed between the phased acoustic array 23 and bases of the well plate reservoirs via the exterior lower surface 19, with the phased acoustic array 23 and the well plate 11 located at a predetermined distance from each other. In some instances the acoustic coupling medium may coat the entire lower surface of the well plate. As depicted in FIG. 4, however, the coupling medium 25 is introduced from a coupling medium source 27 via dispenser 29 to selectively coat the lower surface 19 where needed. As the phased acoustic array is adapted for displacement with respect to the lower well plate surface 19 in the directions indicated by arrow X, the dispenser 29 is depicted in FIG. 4 as located adjacent to the leading surface of the phased acoustic array 23. Also as depicted in FIG. 4, an optional collector 31 is employed to collect coupling medium that may drip from the lower surface 19. As the collector 31 is depicted as containing the coupling medium source 27, it is evident that the coupling medium may be reused. Other means for introducing and/or placing the coupling medium may be employed as well.

The acoustic coupling fluid is preferably an acoustically homogeneous material in conformal contact with both the phased acoustic array 23 and the exterior lower surface 19 of the well plate. In addition, it is important to ensure that the fluid medium is substantially free of material having different acoustic properties than the fluid medium itself. Furthermore, it is preferred that the acoustic coupling medium be comprised of a material having acoustic properties that facilitate the transmission of acoustic radiation without significant attenuation in acoustic pressure and intensity. Also, the acoustic impedance of the coupling medium should facilitate the transfer of energy from the coupling medium into the container.

The device also includes an acoustic ejector 33 comprised of a single acoustic radiation generator 35 for generating acoustic radiation, and a focusing means 37 for focusing the acoustic radiation at a focal point within the fluid from which a droplet is to be ejected, near the fluid surface. As shown in FIG. 4, the focusing means 37 is comprised of a single solid piece having a concave surface 39 for focusing acoustic radiation generated by the acoustic generator 35, but the focusing means may be constructed in other ways as discussed above. The acoustic ejector 33 is thus adapted to generate and focus acoustic radiation so as to eject a droplet of fluid, for example, from each of the fluid surfaces 14AS, 16AS, and 18AS when acoustically coupled to wells 13A, 15A, and 17A, and thus to fluids 14A, 16A and 18A, respectively. The acoustic radiation generator 35 and the focusing means 37 typically function as a single unit controlled by a single controller, but may be independently controlled, depending on the desired performance of the device. Single ejector designs are preferred over multiple ejector designs because accuracy of droplet placement and consistency in droplet size and velocity are more easily achieved with a single ejector.

As depicted, ejector 33 indirectly contacts the well plate via an acoustic coupling medium so as to establish the required acoustic coupling relationship for acoustic ejection. One skilled in the art will recognize that techniques for such indirect contact as described above in the context of acoustic assessment can be readily adapted for acoustic ejection. For example, the ejector 33 and phased acoustic array 23 may, as depicted in FIG. 4, both be acoustically coupled to the well plate 11 via the same fluid-acoustic coupling medium 25. In this instance, the ejector 33 and the phased acoustic array 23 are maintained at substantially the same distance from each other. Alternatively, the ejector and the phased acoustic array may be independently coupled to the well plate (not shown).

Also as depicted in FIG. 4, an optional blade 41 is provided that conforms to the lower exterior surface 19 of the well plate. Such a blade operates on the same principle employed when a windshield wiper or a squeegee is slid across a surface through the application of appropriate pressure to effect water removal. Furthermore, the coupling medium may be removed through the use of an absorbent material through wiping or blotting action. In addition, as depicted in FIG. 4, a vacuum dryer 43 may be used to remove any coupling medium from the lower exterior surface 19 of the well plate. As depicted, the vacuum dryer is comprised of a vacuum table 45 in fluid communication with a vacuum pump 47. Once acoustic analysis and optional ejection has taken place from the well plate, the well plate may be placed on the table so as to remove any remaining coupling medium therefrom. One skilled in the art will recognize that other fluid removal technologies may be used in conjunction with the invention as well.

Figure 5:
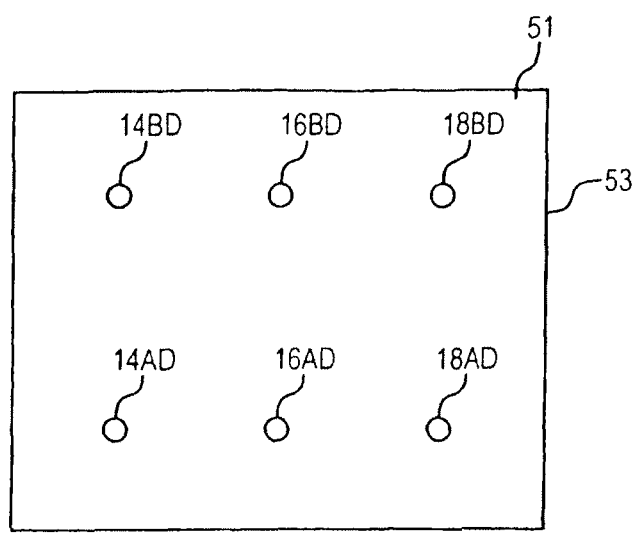
FIG. 5 schematically illustrates a substrate having an array of droplets deposited thereon using the device depicted in FIG. 4.

The device depicted in FIG. 4 may be employed to deposit an array of droplets on a substrate. FIG. 5 depicts an exemplary droplet array that may be formed using the inventive device. As shown, the droplet array is formed from six droplet features indicated at 14AD, 14BD, 16AD, 16BD, 18AD, and 18BD on a substantially planar surface 51 of substrate 53. Droplet features 14AD, 14BD, 16AD, 16BD, 18AD, and 18BD are ejected from the fluids in reservoirs 13A, 13B, 15A, 15B, 17A, and 17B, respectively.

FIG. 6 schematically illustrates the device depicted in FIG. 4 in operation to eject droplets of fluid to form the droplet array depicted in FIG. 5. As shown in FIGS. 6A-6C, a combination positioning means 61 is provided and serves to position the phased acoustic array 23 in acoustically coupling relationship to the lower well plate surface 19. The combination positioning means 61 also serves to move the phased acoustic array 23, the ejector 33, and the blade 41 in the directions indicated by arrow X. In addition, as shown in FIGS. 6E and 6F, the ejector 33 may be moved in the directions indicated by arrow Y by ejector positioning means 63. As shown in FIGS. 6A-6C, the phased acoustic array 23, the ejector 33, and the blade 41 are generally maintained at the same distance from each other. In FIG. 6A, the phased acoustic array 23 is in position to assess the contents of reservoirs 13A and 13B. The acoustic radiation will be reflected under different circumstances. Typically, reflection will occur when there is a change in the acoustic property of the medium through which the acoustic radiation is transmitted. It has been observed that a portion of the acoustic radiation traveling upward will be reflected from the reservoir bases 13AB and 13BB as well as the free surfaces of the fluids contained in the reservoirs 13A and 13B. Thus, for example, low energy acoustic radiation may be generated by the phased acoustic array 23 to assess the volume of fluid contained in reservoirs 13A and 13B. By determining the time it takes for the acoustic radiation to be reflected by the fluid surface back to the phased acoustic array 23, and then correlating that time with the speed of sound in the fluid, the distance—and thus the fluid height and the fluid volume—may be calculated. Of course, care must be taken in order to ensure that acoustic radiation reflected by the interface between the reservoir bases and the fluids is discounted.

Figure 6A:
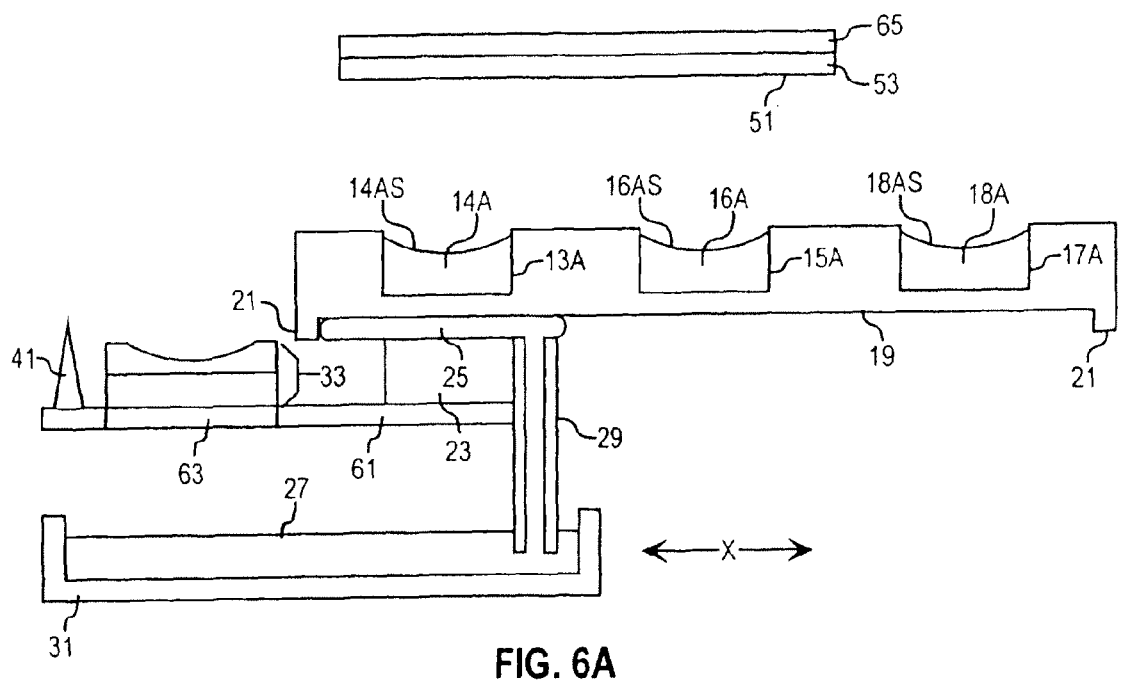
FIGS. 6A-6F, collectively referred to as FIG. 6, schematically illustrate the device depicted in FIG. 4 in operation to eject droplets of fluid to form the droplet array depicted in FIG. 5.
Figure 6B:
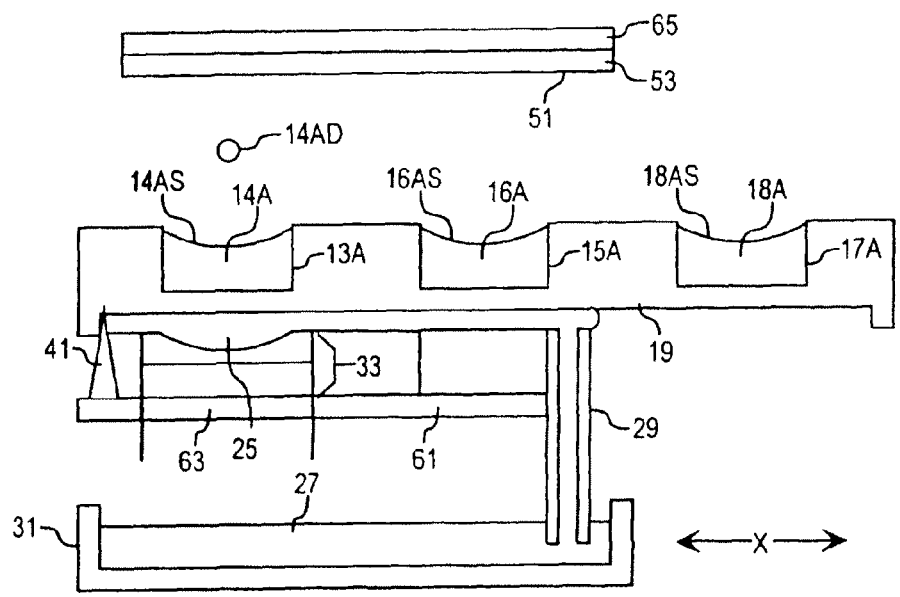

Once the contents of reservoirs 13A and 13B have been assessed, the combination positioning means, as depicted in FIG. 6B, moves the phased acoustic array 23 in position to assess the contents of reservoirs 15A and 15B. Simultaneously, the ejector 33 is positioned in alignment with reservoirs 13A and 13B. As a result, the ejector 33 may eject a droplet of fluid from either or both reservoirs 13A and 13B, depending on the assessment made using the phased acoustic array 23 in FIG. 6A. In some instances, historical droplet ejection data associated with the ejection sequence may be employed as well to determine whether and/or how fluid should be ejected from any of the reservoirs.

In order to form the droplet array shown in FIG. 5, droplets should be ejected from each of the reservoirs. To eject a droplet of fluid from reservoir 13A, the ejector positioning means 63, as depicted in FIGS. 6B and 6E, may position the ejector 33 directly below reservoir 13A and in acoustic coupling relationship therewith through acoustic coupling medium 25. In addition, a substrate positioning means 65 positions the substrate 53 such that substrate surface 51 is in appropriate droplet receiving relationship to reservoir 13A. Once the ejector, the reservoir, and the substrate are in proper alignment, the acoustic radiation generator 35 is activated to produce acoustic radiation that is directed toward the free fluid surface 14AS of the reservoir 13A. The acoustic radiation will then travel in a generally upward direction toward the free fluid surface 14S. As a result, droplet 14AD is ejected from the fluid surface 14AS onto a designated site on the underside surface 51 of the substrate 53. The ejected droplet may be retained on the substrate surface by solidifying thereon after contact; in such an embodiment, it may be necessary to maintain the substrate at a low temperature, i.e., a temperature that results in droplet solidification after contact. Alternatively, or in addition, a molecular moiety within the droplet attaches to the substrate surface after contact, through adsorption, physical immobilization, or covalent binding.

Then, the substrate positioning means 65 repositions the substrate 53 over reservoir 13B in order to receive a droplet therefrom at a second designated site. FIG. 6F shows that the ejector positioning means 63 has repositioned ejector 33 below reservoir 13B. Once properly aligned, the acoustic radiation generator 35 of ejector 33 is again activated to eject fluid from reservoir 13B.

Figure 6C:
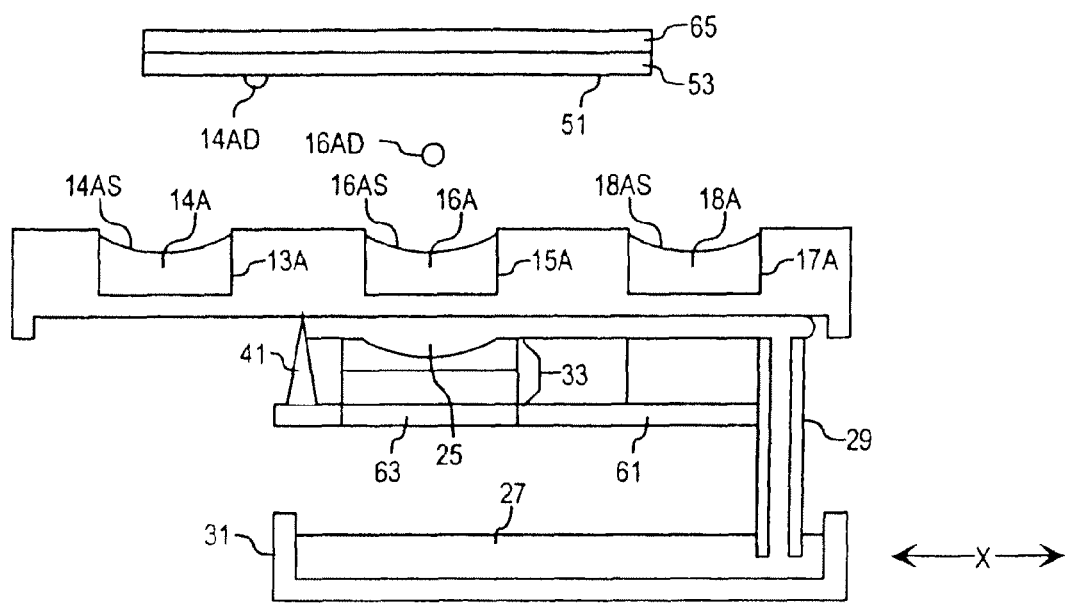
Figure 6D:
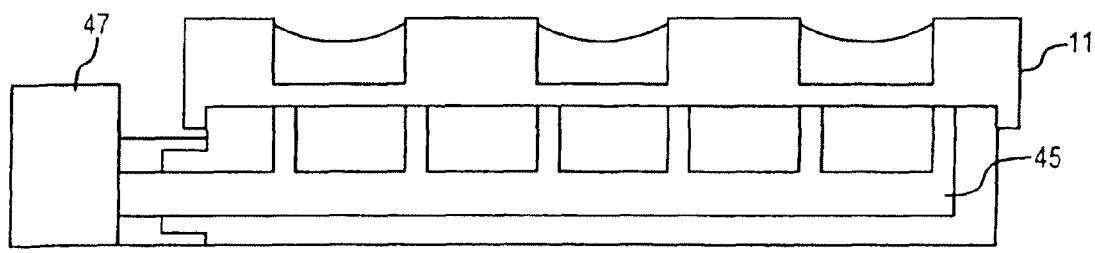
Figure 6E:
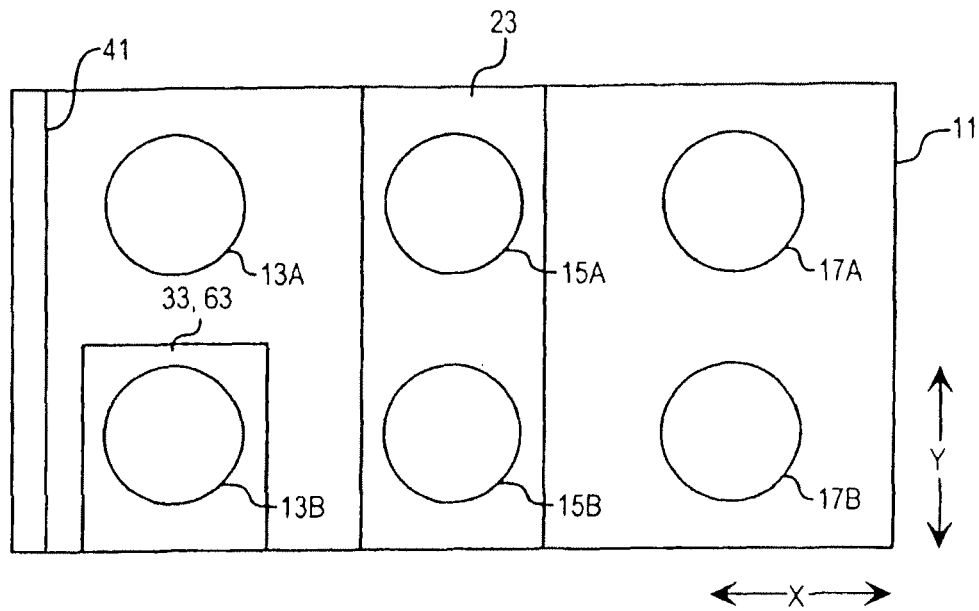
Figure 6F:
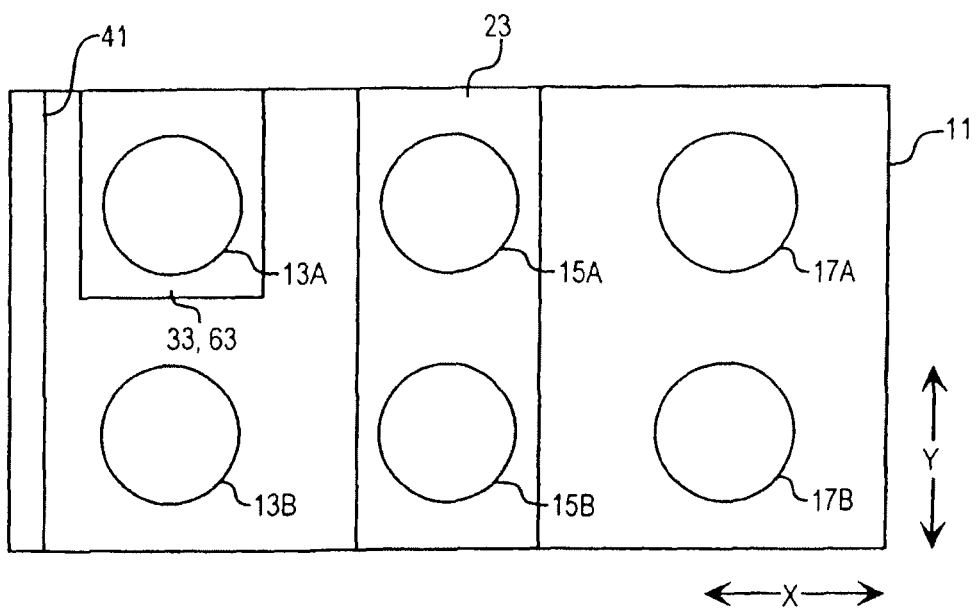

In FIG. 6C, the droplet 67 has been deposited as a droplet feature on substrate surface 53, and the phased acoustic array 23 is positioned by combination positioning means 61 in position to assess the contents of reservoirs 17A and 17B. Similarly, the ejector 33 is positioned in alignment with reservoirs 15A and 15B. Also depicted in FIG. 6C is the ejection of a droplet 16AD of fluid from reservoir 15A. As acoustic coupling medium 25 is no longer needed directly beneath reservoirs 13A and 13B, blade 41 is moved by the combination positioning means 61 to direct acoustic coupling medium from the well plate surface 19 into collector 31. Once the droplet array is completed on substrate surface 51, the well plate 11 is placed on vacuum table 45 to ensure that all acoustic coupling medium is removed from the well plate 11, as depicted in FIG. 6D. It will be appreciated that various components of the device may require individual control or synchronization to form an array of droplets on a substrate. For example, the ejector positioning means may be adapted to eject droplets from each reservoir in a predetermined sequence associated with an array of droplets to be prepared on a substrate surface. Similarly, the substrate positioning means for positioning the substrate surface with respect to the ejector may be adapted to position the substrate surface to receive droplets in a pattern or array thereon. Either or both positioning means, i.e., the ejector positioning means and the substrate positioning means, may be constructed from, for example, motors, levers, pulleys, gears, a combination thereof, or other electromechanical or mechanical means known to one of ordinary skill in the art. It is preferable to ensure that there is a correspondence between the movement of the substrate, the movement of the ejector, and the activation of the ejector to ensure proper array formation.

Accordingly, the invention relates to the assessment of the contents of a plurality of reservoirs as well as to dispensing a plurality of fluids from reservoirs, e.g., in order to form a pattern or an array on the substrate surface 51. However, there are a number of different ways in which content assessment and fluid dispensing may relate to each other. That is, a number of different sequences may be employed for assessing the contents of the reservoirs and for dispensing fluids therefrom. In some instances, the contents of a plurality of reservoirs may be assessed before fluid is dispensed from any of the reservoirs. In other instances, the contents of each reservoir may be assessed immediately before fluid is dispensed therefrom. The sequence used typically depends on the particular fluid-dispensing technique employed as well as the intended purpose of the sequence.

As discussed in U.S. Patent Application Publication No. 20020037579 to Ellson et al., focused acoustic radiation may be used to eject fluid droplets toward discrete sites on a substrate surface for deposition thereon, as well as to transfer fluids from one set of containers into another set of containers. For certain diagnostic applications or preparations of diagnostic materials, it would be desirable to use the same acoustic assessment device to assess the contents of reservoirs from which fluids are dispensed and to determine whether droplets are properly received on the substrate. Thus, it should be apparent that when the invention is employed to deposit droplets on a surface, the invention may be further employed to interrogate the substrate to assess the contents and/or location of the droplets on the substrate surface Thus, the present invention represents a significant improvement over known technologies relating to the acoustic assessment of the contents of a plurality of reservoirs. Unlike previously known acoustic assessment technologies that require a sensor in direct contact with a fluid in a reservoir be assessed, the invention allows for assessment of the contents of a plurality of containers without direct contact with the contents of the containers. In addition, unlike non-contact acoustic systems such as those described in U.S. Pat. No. 5,880,364 to Dam, direct measurements are made that may provide information relating to the volume as well as the properties of the fluids in the reservoir. This use of fluid acoustic coupling media overcomes low acoustic impedance problems associated with technologies that rely on gaseous materials for acoustic coupling. Accordingly, the present invention represents a more energy efficient technology that may be employed to provide more accurate and detailed assessment of the contents of a plurality of fluid reservoirs. Some of this additional accuracy can be achieved by using higher frequency acoustic waves (and hence shorter wavelengths), as these acoustic waves can be transmitted effectively through liquids yet would be very rapidly attenuated in air.

In addition, acoustic assessment is a generally noninvasive technique that may be carried out regardless of whether the reservoirs are sealed or open. That is, acoustic assessment does not require extracting a sample for analysis or other mechanical contact that may result in sample cross-contamination. In addition, unlike optical detection techniques, optically translucent or transparent reservoirs are not required. This, of course, provides a wider range of choices for material that may be employed for reservoir construction. In addition, the use of opaque material would be particularly advantageous in instances wherein the reservoirs are constructed to contain photosensitive fluids.

As another example, the invention may be employed to detect whether the contents of a sealed reservoir are at least partially frozen without opening the reservoir. This would be useful when it is known that a reservoir contains a substance that is capable of existing as a fluid over a temperature range, but it is unclear as to the temperature history of the reservoir, e.g., whether freeze thaw cycles existed. For example, water is capable of existing as a fluid at a temperature of about 0° C. to about 100° C. If it is unclear whether the exterior temperature of a reservoir is indicative of the reservoir's interior temperature, but the reservoir is known to contain liquid water, the inventive device is well suited to determine whether any or all of the contents of the reservoir is a fluid.

Furthermore, the inventive device may be constructed to be highly compatible with existing infrastructure of materials discovery and with existing automation systems for materials handling. For example, the invention may be adapted for use as an alternative or a supplement to content assessment means that are based on optical detection. In some instances, sonic markers may be provided in the reservoirs to identify the contents of the reservoir. Thus, the invention may be employed as a means for inventory identification and control in a number of contexts, including, but not limited, to biological, biochemical, and chemical discovery and analysis. In particular, the invention is particularly suited for use in assessing the contents of reservoirs containing pharmaceutical solutions.

In a further embodiment of the invention, acoustic radiation is used to determine parameters of a fluid which are relevant to the performance of acoustic ejection. Preferably, this determination uses the same equipment that will be employed for the acoustic ejection itself.

Among the parameters which are relevant to acoustic ejection are the speed of sound in the fluid and the viscosity.

We discuss first the measurement of the speed of sound, since the result of that measurement is needed for other purposes, for example, to ascertain the volume of fluid in a reservoir. To measure the speed of sound in the fluid of interest, a first method would be to (i) measure a known amount of fluid into a reservoir (for convenience of exposition assumed to be oriented facing upwards), (ii) measure the location of the top of the fluid relative to the bottom of the fluid in the reservoir, and (iii) send a toneburst of acoustic radiation from a transducer below the reservoir upwards through the fluid towards its top, and (iv) measure how long it takes for the echo of the toneburst from the top of the fluid to return to the transducer.

To be more specific, the transit time of a sound wave in a material is the distance that acoustic radiation travels through that material divided by the speed of sound c in that material. The toneburst used to measure the speed of sound as just described would potentially pass through a number of materials on its way from the transducer to the top of the fluid in the reservoir. In an exemplary acoustic ejection system, it could pass through a lens which focuses the acoustic radiation, a coupling medium which couples the radiation to the reservoir, the reservoir itself, and then the fluid in the reservoir.

One simple way to measure the speed of sound, if the depth of the fluid in the reservoir is known, is to detect at the transducer the echoes from the reservoir-fluid interface and from the top of the fluid when a toneburst of acoustic radiation is sent into the fluid in an upwards direction. The time difference between those two echoes is twice the one-way transit time of the acoustic radiation through the fluid. The speed of sound may be computed dividing the depth of the fluid by the one-way transit time.

In a variation on the method just described, instead of detecting the echo from the reservoir-fluid interface, one could (i) compute the transit time T' through the materials that the acoustic radiation toneburst traverses prior to entering the fluid from known dimensions and properties of those materials, and (ii) subtract this computed transit time from the transit time T of the toneburst from transducer to the top of the fluid, determined by detecting the echo of the toneburst from the top of the fluid.

The direct measurement of the depth of the fluid in a reservoir may be time consuming or clumsy. A second preferred method for measuring the speed of sound in an unknown fluid, which avoids the need for such measurement of fluid depth, is as follows: (i) immerse a solid object in the fluid, the solid object being immersed at a known distance from the bottom of the reservoir, (ii) send a toneburst of acoustic radiation from a transducer below the reservoir upwards through the fluid towards the immersed object, and (iii) measure the time T which it takes for the echo of the toneburst from the immersed object to return to the transducer. From the time T, one subtracts the time T' taken traveling between the transducer and the bottom of the fluid in the reservoir, and thus obtains the transit time between the bottom of the fluid and the immersed object. If the distance between these two is known, one can then obtain the speed of sound easily. T' may be determined as discussed above.

It is common for acoustic ejection systems to have means to carry out the precise positioning of an object relative to the fluid reservoir in the vertical direction, which for convenience we will call the z direction. This precise positioning can be used to automatically place the solid object at a known distance from the bottom of the reservoir if the z position of the bottom of the reservoir is known with adequate precision. This precise positioning ability obviates the need to measure directly the depth of the fluid itself.

An alternative preferred technique for measuring the speed of sound in a fluid is (i) to position a solid object within the fluid in the reservoir at two z positions separated by a known distance d, and (ii) to detect the echoes of a toneburst from the solid object at those two positions. If those echoes occur at times $T_1$ and $T_2$ after the toneburst is generated, it may be inferred that sound traverses a distance d in the fluid in a time $\frac{1}{2}(T_1-T_2)$, so that the speed of sound is $2d/(T_1-T_2)$. This allows estimation of the speed of sound without knowing the exact z location of the bottom of the fluid in the reservoir. The distance d is preferably a few millimeters.

In the determination of the speed of sound it is desirable to use focused acoustic radiation, which is the type of radiation that is generally available from transducers used for acoustic ejection. In that case it is desirable to make a correction to the speed of sound calculation taking into account the focus of the radiation. Corrections of this type are discussed generally in G. S. Kino, *Acoustic waves: Devices, imaging and analog signal processing* (Prentice Hall 1987).

In the performance of the methods just described, a wide variety of immersed solid objects may be employed. However, it is preferable that the immersed solid object have an acoustic impedance sufficiently different from that of the fluid that the reflected echo signal is strong enough to be readily distinguished from background and other echoes. A useful solid object for this purpose would be a disposable pin tool of a type commonly used in fluid transfer applications, such as a VP248 (V&P Scientific, San Diego, Calif.), which has 12 mm long pins with a tip diameter of 1.0 mm and is made of polypropylene. In an acoustic ejection system, it is common to have a target or destination position above the source reservoirs into which a disposable pin tool of this kind can be loaded. Z positioning of the reservoirs or of the disposable tool will then accomplish the immersion called for by the methods described above.

The methods just described may also be carried out with acoustic radiation directed along a non-vertical direction. When doing so, it is useful to be able to position the immersed object precisely in the direction along which the acoustic radiation is directed.

The experimental determination of viscosity may be carried out with the use of ultrasound. A technique which may be used is to send a toneburst to the fluid surface along the z direction with sufficient energy to cause significant oscillation in the fluid surface. Following this toneburst, a series of further tonebursts, preferably at lower energy and of brief duration, is sent to the fluid surface to interrogate the position of the fluid surface. Preferably, 100 or more such further tonebursts are sent. For each such further toneburst, an echo delay is determined. An exponentially damped sinusoid or other exponentially damped curve is fitted to the curve of echo delay versus time resulting from the series of echo delays so determined. The exponential decay time of the fitted exponentially damped curve is then compared with the decay time observed in a similar experiment for a fluid of known viscosity. The known viscosity is multiplied by the ratio of the exponential decay time for the fluid of interest divided by the exponential decay time for the known fluid to give the viscosity of the fluid of interest.

Figure 10:
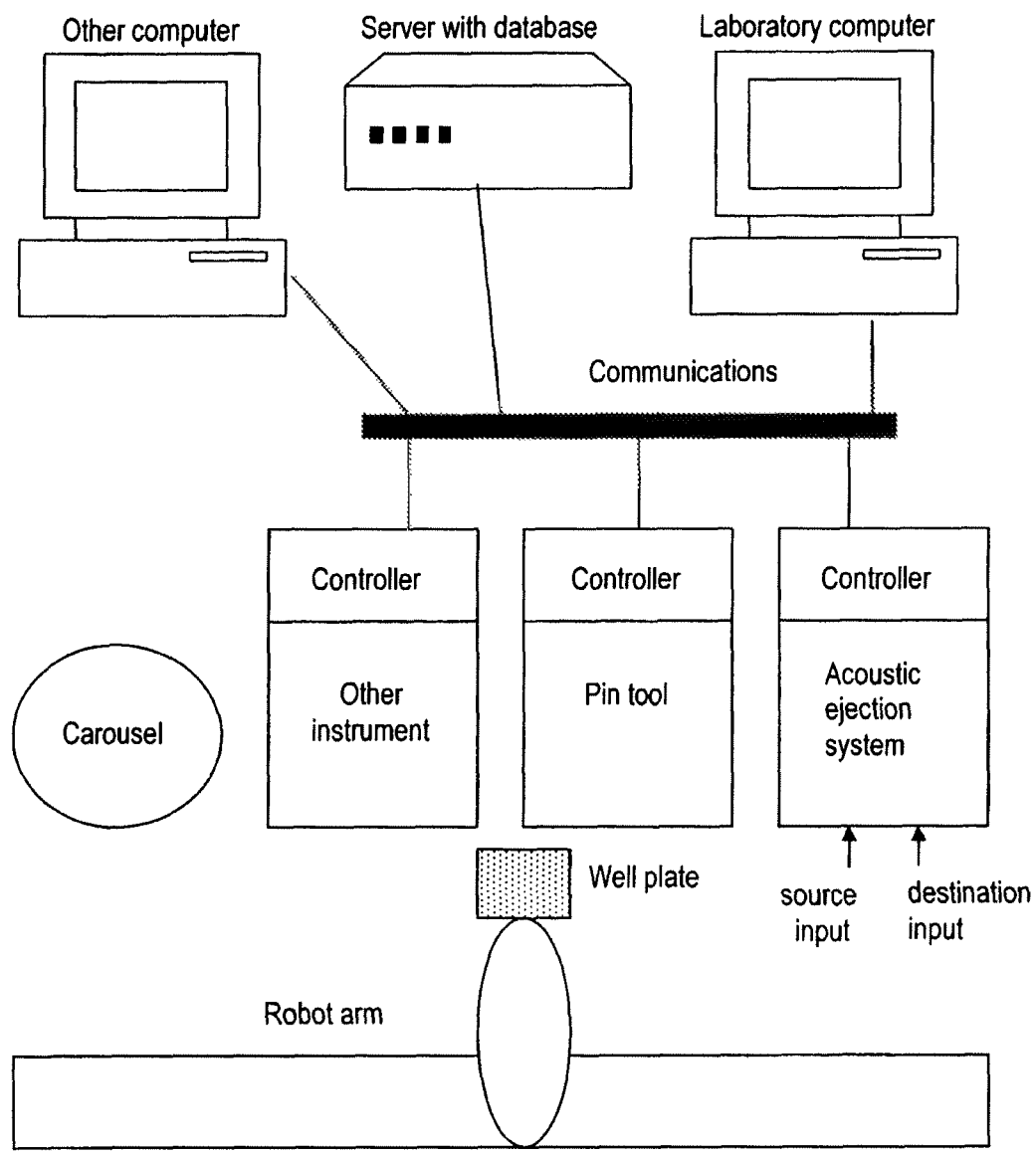
FIG. 10 depicts a laboratory automation environment which could be suitable for carrying out some of the methods of the invention.

The steps of methods previously described, with the possible exceptions of the insertion of the reservoir with fluid and of the immersible solid object into the acoustic ejection system, may be programmed into the controller of a typical acoustic ejection system. Such a controller may comprise a computer or similar microprocessor based system which executes software or firmware, possibly assisted by one or more microprocessors designed specifically to perform algorithms of digital signal processing (DSP) or having particular advantages for the performance of such algorithms. Such a controller may also comprise communications hardware, for example a network interface, and corresponding software, to communicate with other laboratory automation equipment and general purpose computers. It will also be understood that certain acoustic ejection systems may possess or be connected to automated handling equipment which is also capable of inserting the reservoir with fluid and immersible solid object under the direction of an electronic controller or similar system, which system may execute software or firmware which contains code designed to carry out the methods previously described. See FIG. 10 for a depiction of an exemplary overall laboratory automation environment in which the methods of the invention may be practiced.

When preparing to perform acoustic ejection on a new fluid, it is common to make use of and adjust acoustic radiation waveforms that have been studied in prior work with other fluids. A wide variety of such waveforms have been studied in the art. Published work includes U.S. Pat. No. 4,308,547 to Lovelady et al, U.S. Pat. No. 5,122,818 to Elrod et al., U.S. Pat. No. 5,808,636 to Stearns, and U.S. Pat. No. 5,912,679 to Takayam et al. Such waveforms may for example consist of one or more pure tones of particular durations and relative spacings, of one or more optionally band-limited white noise pulses of particular durations and relative spacings, or of one or more linear chirps of particular starting and ending frequencies and durations and relative spacings. A suitable general class of toneburst waveforms for ejection consists of two or three linear chirps, not having identical frequency characteristics, separated in time by an interval which is preferably in the tens or hundreds of microseconds depending on observed characteristics of the ejection process.

To build on the prior work done with other fluids, one records for each of a number of such fluids the waveforms and acoustic energy levels which have given rise to particular droplet volumes, as well as physical parameters of those fluids. One then characterizes the new fluid through a set of physical parameters, for example viscosity and speed of sound, and uses those physical parameters plus the desired droplet volume to interpolate or extrapolate the parameters of waveforms from those which have already been determined to eject droplets of known volume.

Different modes of interpolation or extrapolation which are known in the art may be used. The interpolation or extrapolation may be performed, for example, by software or firmware being executed in the controller of an acoustic ejection system which has been provided with information about the previously studied fluids. The interpolation or extrapolation gives a starting point for experimental adjustment of parameters to ultimately achieve ejection of the desired droplet dimensions.

A situation may arise in which the new fluid is similar to previously studied fluids in that it is like a previously studied fluid mixture but with different percentages of each component. In that case, it may be preferable, rather than interpolating or extrapolating on the basis of physical characteristics of the fluid, to interpolate or extrapolate based on the percentages of each component. Likewise, the new fluid may be similar to previously studied fluids in that it is a solution with the same solvent and solute as a previously studied fluid, but with different concentrations of the solute. In that case the concentration of the solute may be a better basis for interpolation or extrapolation than physical characteristics of the fluid.

This method of using prior knowledge to adjust waveforms previously used to eject droplets is particularly adapted to be performed automatically under the control of the controller of an acoustic ejection system, although the method also can be carried out with manual intervention. Preferably such a controller would contain programming, e.g., by software or firmware, which would direct the operation of the acoustic ejection system.

In seeking to eject droplets of a new fluid, an important consideration is the level of acoustic energy to be employed for ejection. Increasing the amplitude will increase the acoustic energy delivered to the vicinity of the free surface. That acoustic energy provides the energy to detach the droplet from the body of the fluid, overcoming forces which oppose such detachment such as surface tension and gravity. The acoustic energy also provides kinetic energy to the droplet.

One way to find a level of acoustic energy suitable for ejecting a droplet of a fluid would be to use a toneburst waveform and energy level and observe visually whether a droplet is ejected. If no droplet is ejected, one would scale up the toneburst energy until ejection occurs. The visual observation may take place through a camera which produces images which may be analyzed by a human or automatically to determine if ejection has occurred. A drawback of this method is the need for a camera which may not be otherwise useful in the acoustic ejection system.

The experimental adjustment of the acoustic energy of a toneburst waveform suitable for ejecting a droplet of a desired volume from a new fluid may alternatively employ the techniques discussed in U.S. patent application Ser. No. 10/956,616 by Stearns et al. That application also discusses the experimental determination of the optimal position of the transducer to eject from a particular volume of fluid held in a particular reservoir.

In the experimental determination of an appropriate acoustic energy level for a new fluid, one would typically place a quantity of that new fluid in a reservoir of known characteristics and connect it to an ultrasonic ejection system. One would check that this level is such as to be ejectable. For example, if the level is so deep that it is impossible to focus near the top of the fluid, the level would generally be too high to be ejectable. If the level is so low that the ejected drop would contain more fluid than is present in the reservoir, the level is too low. Preferably for purposes of testing, the level of fluid in the reservoir is well below the highest point at which the acoustic ejection system can focus acoustic energy and contains a number of times the expected or desired volume of the droplet. It should be noted that despite these limitations, it is possible to perform the steps of the methods suggested here for determining an acoustic energy level with small quantities of the new fluid, for example with 50 uL or 10 uL or 5 uL or even less, because the methods do not involve much actual ejection of fluid and because in any event the ejected droplets are likely to be, for typical waveforms with frequencies in the 5 to 10 MHz range, quite small, on the order of tens of nanoliters. For waveforms with frequencies above 30 MHz, ejected droplets may be volumes substantially smaller than a nanoliter and could even be a picoliter or lower.

For the experimental calibration of the appropriate energy content of a waveform in accordance with application Ser. No. 10/956,616 one might perform the following steps. One would scale the waveform obtained by interpolation or extrapolation as explained above back to a relatively low level which one feels reasonably confident, based on the interpolation or extrapolation, would not be sufficient to eject a droplet. One would then generate the scaled back waveform using a suitable controller and ultrasound transducer and send it to a focus one to five wavelengths below the top surface of the fluid. Some time thereafter, for example a few hundred microseconds, one would send a probe pulse to the fluid surface. Preferably the probe pulse is brief, for example, one or two cycles, preferably at the transducer center frequency. Likewise, the probe pulse preferably has sufficiently low power so as not to significantly perturb further the fluid surface.

The echo from the probe pulse would optionally be isolated by filtering or otherwise from other inputs sensed by the transceiver. The echo would then be subjected to a Fourier-type transform algorithm such as a Fast Fourier Transform (FFT). A Fourier-type transform algorithm is any algorithm which reaches a result which can be calculated by a technique which includes a step which performs or approximates a discrete or continuous convolution of the sample data with a complex exponential function of a discrete or continuous variable. Such algorithms include for example the Discrete Fourier Transform (DFT).

It has been determined empirically, as discussed in application Ser. No. 10/956,616, that there is a relationship $E_T = A \times \ln(\text{min\_spacing}) + B$ where $E_T$ is difference between the toneburst energy and the ejection threshold and min_spacing is the difference in MHz (or some other convenient unit of frequency) between two minima of the FFT-transformed echo waveform. The values A and B vary somewhat with the fluid. Exemplary values of A and B measured for a mixture of 70% DMSO and 30% water would be 0.44 and 0.49, giving an $E_T$ in decibels where min_spacing is expressed in MHz.

If a min_spacing is measured for the new fluid, the relationship noted can be used to determine an approximate ejection threshold for that fluid. That approximate ejection threshold can be used to determine the energy of the toneburst suitable for ejecting a droplet of the new fluid. The toneburst energy could be, for example, 0.5 dB, 1.0 dB, or 1.5 dB above the approximate ejection threshold. The A and B values used to determine the approximate ejection threshold should be those of a fluid with similar viscosity, surface tension, and/or speed of sound, or may be interpolated or extrapolated from values for a number of such fluids based on the values of the viscosity, surface tension, and/or speed of sound for the new fluid.

Once one has determined an energy and an interpolated or extrapolated waveform for a test toneburst intended to eject a droplet of the new fluid, one can apply that test toneburst to the fluid. In doing so, it is convenient to employ the position optimization technique described in application Ser. No. 10/956,616. Briefly, that technique consists of determining min_spacing as described above for a fixed toneburst waveform and energy and for a number of positions of the focus to which the toneburst is directed, and on the basis of those determinations selecting a position of the focus which produces the lowest min_spacing.

After one has applied the test toneburst to the fluid, one can visually observe whether a droplet is being ejected. Alternatively, for more automatic operation, one may capture digital images of the ejection process with a digital camera and by human or automatic analysis of the digital images determine that ejection is taking place. Alternatively, one can subject the fluid to the test toneburst repeatedly and see if that has a proportionate effect on the level of fluid in the reservoir. Alternatively, one can (a) send the test toneburst out in an arrangement where any droplets which are ejected will be captured in a further reservoir. This reservoir could be either empty or filled to a known level. After sending the test toneburst out a large number of times, for example 200 to 1000 times, one can (b) use acoustic energy to determine the level of fluid in the further reservoir and (c) see if that level of fluid is proportionate to the number of test tonebursts. If these tests show that ejection is not occurring, one may increase the energy of the test toneburst gradually and see if ejection eventually occurs with some energy which the transducer is capable of producing for the selected waveform.

Another way to ascertain acoustically whether a droplet has been ejected by a test toneburst is to use probe pulses to ascertain if ejection has occurred. This method has the advantage over the preceding methods, which involve repeated ejection, that it takes less time, does not consume significant quantities of the new fluid and is suitable when small volumes of the fluid are available or the fluid is expensive.

In seeking to detect ejection taking place acoustically, one examines the echoes of a plurality of probe pulses following the test toneburst, for example fifty probe pulses spaced 200 µs apart. As a test toneburst is scaled up in power from below the ejection threshold to above the ejection threshold, the pattern of echoes of the probe pulses varies as depicted in FIGS. 9A-9H. In those figures, the vertical axis of the graph is time in nanoseconds (ns), with time advancing in the downward direction. The horizontal axis gives the numbers of the probe pulses, which in the experiments that led to the figure were spaced 200 µs apart and were very brief (about one cycle). Grayscale intensity within the graph indicates the value of the acoustic signal received by the transceiver. The power is measured relative to the ejection threshold, so that for example 0.0 dB means that the test toneburst was at the ejection threshold. As may be seen, as the power of the test toneburst is scaled up, there appears a short principal echo from each probe pulse and a series of further echoes, which may have greater amplitude than the principal echo. As may be seen, the further echoes die out relatively quickly when the power is below ejection threshold and last considerably longer when the power is above ejection threshold. The duration of the further echoes as one steps up in power is thus seen to be usable to discriminate between conditions in which ejection takes place and does not take place.

An alternative way to discriminate the power regions below and above ejection is also seen in FIGS. 9A-9H. In the region below ejection threshold, the further echoes are in the shape of a shallow U and rejoin the principal echo as time advances. In the region above ejection threshold, the further echoes generally do not rejoin the principal echo but rather simply peter out. In FIGS. 9A-9H it may be seen that the rejoining and/or petering out occur at approximately 15 probe pulses into the process, i.e., about 3 ms after the test toneburst.

In the interpretation of patterns of echoes as depicted in FIGS. 9A-9H it is useful to keep in mind the following. The test toneburst will in general cause the surface of the fluid to develop a mound above the focus point. Above this mound, if the acoustic energy is sufficient, there will form a projection of very roughly acoustic wavelength diameter. With adequate energy, a droplet will pinch off from that projection and proceed upward, having thus been ejected. The vestiges of the projection and the mound will then (on a timescale of milliseconds or tens of milliseconds) sink back to the level of the bulk of the fluid. The rejoining of the shallow-U-shaped further echoes and the principal echo corresponds to the mound settling back down. The petering out of the further echoes corresponds to the droplet pinching off from the projection. At higher power levels, a pinch off may be followed by a shallow U from what remains of the projection.

In the implementation of the methods just described for ascertaining acoustically whether a droplet has been ejected by a test toneburst, one may use an image-pattern matching algorithm that compares the echo image from an event to a "library" of images associated with known ejection events. This pattern matching technique could also with a suitably library be used to determine the difference between the test toneburst's energy and the ejection threshold energy, whether multiple droplets formed, or whether a drop fell back into the reservoir.

Where test toneburst waveforms are used which have discrete segments (e.g., tones or chirps) separated by a time interval, the pattern of the echoes may be affected by the existence of the separate segments. The echo pattern may not precisely follow that of FIGS. 9A-9H in the middle of the echo. However, the portion of the echo pattern where the further echoes rejoin the principal echo should in general have the form of the pattern in FIGS. 9A-9H.

The method of determining a suitable energy level for a given waveform does not take a great deal of time to perform. Ejections can be done, as noted elsewhere, at rates of at least 10 per second, and potentially even 100 per second. Where ejections are being carried out against the same reservoir, and do not involve mechanical motion of the acoustic radiation generator, they may be carried out even more rapidly. The test tonebursts here take a similar time to an actual ejection. It may be expected that a suitable energy level will be determinable with no more than thirty-five test tonebursts: (a) two to measure speed of sound, (b) three to measure up to three additional characteristics of the fluid such as viscosity for purposes of interpolation or extrapolation, (c) ten to determine a value of the "A" coefficient correlating min_spacing with energy, (d) ten to determine the position of the focus which produces the lowest min_spacing, and (e) if ejection is not achieved immediately with the energy predicted by use of the formula $E_T = A \times \ln(\text{min\_spacing}) + B$, ten more to advance upward in energy until ejection is achieved. With 10 test tonebursts per second, the determination of an acoustic energy would take only 3.5 seconds plus an additional 100 ms after each of the tonebursts of part (b) to allow some additional time to make a good determination of damping coefficients, for a total of 3.8 seconds. If the tonebursts can be issued at 100 per second, still leaving an extra 100 ms after each toneburst of part (b), the total time would be 650 ms.

In a further embodiment of the invention, once one has ascertained for a particular fluid an acoustic waveform which is capable of ejecting a droplet, one can measure the size of the ejected droplet by seeing the effect that ejecting one or more droplets with that acoustic waveform has on the level of fluid in a further reservoir into which the droplet is ejected. For carrying out a measurement of this kind, it is preferable that the dimensions of this further reservoir be known, particularly its cross section perpendicular to the vertical direction. It is preferable that the further reservoir be cylindrical. It is preferable to use a fairly large number of droplets, for example 200 to 1,000, so as to have a readily measurable effect on the fluid level of the further reservoir. This number could be larger or smaller depending on the relative size scale of the droplet and the cross sectional area of the reservoir. Preferably, the fluid level in the further reservoir is measured by means of acoustic radiation, and the cross section is used together with the level information to calculate the amount of fluid in the further reservoir. Potentially, the level of fluid is measured at different points within the further reservoir so as to account for any possible meniscus effect. The measurement of the fluid level in the further reservoir may be carried out within a single acoustic ejection system by repositioning the further reservoir so that it is in an appropriate position for the acoustic radiation generator to send acoustic radiation into it. If the acoustic ejection system has positions for source and destination well plates, the well plate containing the further reservoir would initially be in the destination position, receiving the ejected droplets. The well plate in the source position would then be removed and placed elsewhere, while well plate with the further reservoir would be moved into the source position so as to determine its fluid level by acoustic measurement.

Once one has determined the droplet size actually achieved by the interpolated or extrapolated waveform at the experimentally determined energy level, one may further alter that waveform, potentially iteratively, in order to closer approximate the droplet size desired. As an example, one may decrease the frequency at which acoustic energy is delivered in order to increase the amount of fluid delivered by the droplet. If a modification m to a waveform parameter is observed to result in a change in droplet volume ΔV which is x times the change in volume needed to achieve the desired final droplet volume, it may be desirable in the next iteration to instead apply a modification m/x to the parameter to get closer to the desired volume.

As discussed in more detail elsewhere, acoustic ejection systems of the invention may have the ability to receive an assembly comprising a plurality of reservoirs, e.g., a well plate, and to direct focused acoustic energy to fluid in any of the reservoirs, preferably through suitable movement of the acoustic energy generator. The techniques discussed here for determining characteristics of a fluid, determining on the basis of information about other fluids a waveform for a toneburst suitable to eject from the fluid, determining an energy level suitable to eject from the fluid, and determining how much fluid has been ejected by a toneburst, may be performed automatically on more than one fluid if more than one fluid is presented to the acoustic ejection system, for example different fluids in different wells of a plate. Thus it would be possible, for example, to perform the analyses described above for a different fluid in each well of a 384-well plate. Certain steps in the process described above could then be accomplished more efficiently for a plurality of wells before proceeding to the next step. For example, the speed of sound could be measured for all wells prior to determining the energy level for droplet ejection for at least one of the wells.

In particular, the process for determining droplet size, which may require a comparatively time-consuming repositioning of the further reservoir in relation to the acoustic radiation generator, may benefit from having the multiple droplet ejection be carried out in parallel on a number of wells in a well plate prior to the repositioning step which measures the level of fluid in the further reservoirs. For a single fluid in a single reservoir it might take ten cycles of 500 ejections to arrive at a suitable volume. The ejection part of the cycles might take, for example, under 1 minute apiece if ejections are done at a rate of ten per second. It might take, depending on the available automated handling equipment, another 2 minutes to reposition the further reservoir that receives the ejected droplets in relation to the acoustic radiation generator and for the level of fluid in the further reservoir to be determined (an operation which by itself could take 1 second or less). Thus, for a single fluid, ten cycles of ejection followed by level measurement would take three minutes apiece, or a total of half an hour to arrive at a droplet volume suitable close to the desired one if ten cycles are needed for that. On the other hand, with ten different fluids on a well plate are being analyzed in parallel, the time to eject 500 droplets of all ten fluids would be 10 minutes, the repositioning of the well plate would still take 2 minutes, and the time to measure fluid depth on the ten wells would still be very limited, well under 0.5 minute. Thus, ten cycles would take 10×12.5 minutes=125 minutes, or 12.5 minutes per fluid versus half an hour if the fluids are treated singly. It should be understood that the number of cycles required may vary, such that it may be possible to perform drop calibration with just two cycles of 500 ejections if there is good linearity between drop volume and the waveform parameter being altered, or in three or four or five such cycles. It should also be understood that the 500 ejection number is exemplary, so that the number of droplets ejected could vary being, for example, 200 or 1000.

Once the process of determining speed of sound and other fluid characteristics, determining a toneburst waveform through interpolation or extrapolation, determining an acoustic energy for ejection, and modifying the waveform to achieve a desired droplet size is done, data collected during the process are preferably added to the collection of data available for subsequent interpolation or extrapolation. The data may be stored in the acoustic ejection system controller itself, or in any laboratory automation or general purpose computer with data communications capability, all under the control of suitable software or firmware. The data collected in this manner may be stored outside a database, in flat files for example, or it may, if one or more of these computers or controllers is equipped with a database management system, be stored in a database.

Variations of the present invention will be apparent to those of ordinary skill in the art. For example, while FIG. 1 depicts the inventive device in operation to form a biomolecular array bound to a substrate, the device may be operated in a similar manner to format a plurality of fluids, e.g., to transfer fluids from odd-sized bulk containers to wells of a standardized well plate. Similarly, while FIG. 2 illustrates that the acoustic radiation generator and the detector are in vertical opposing relationship, other spatial and/or geometric arrangements may be employed so long as acoustic radiation generated is transmitted through at least a portion of the reservoir to the detector.

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains.

All patents, patent applications, journal articles, and other references cited herein are incorporated by reference in their entireties.

The following examples are put forth so as to provide those of ordinary skill in the art with a complete disclosure and description of how to implement the invention, and are not intended to limit the scope of what the inventors regard as their invention.

EXAMPLE 1

Measurements were made to determine the usefulness of acoustic echoing to carry out in situ measurement of fluid properties. About 45 uL of fluid comprised of a solution containing 70% DMSO and 30% water was pipetted into a well of a polypropylene well plate containing 384 wells. The fluid exhibited a concave fluid surface in the well. A transducer was aligned at approximately the center of the well and the transducer height was optimized for ejection. A toneburst was applied to the fluid as to perturb the fluid surface and to produce a subthreshold ejection cone. A toneburst was then applied to the transducer (10 MHz, F #2), of 10 MHz center frequency, and of energy approximately 1.5 dB below ejection threshold. The initial cone produced contained many spatial frequencies, which propagated as capillary waves outward toward the well walls. Then, the waves were partially reflected from the well walls through the center of the well, toward the opposing well walls, again reflected, and so on. In other words, the capillary waves reverberated radially within the well. While capillary waves are generally considered dispersive because waves of different wavelength travel at different speeds, this reverberation is somewhat different from, but can nevertheless be reasonably approximated as corresponding to a dispersive membrane.

After the toneburst was applied, a series of echo pulses were generated to monitor the perturbation of the fluid surface. An echo pulse was generated every 200 microseconds, and three hundred pulses were generated in all. The reflected acoustic signals were logged, in the time window of 25 microseconds to 40 microseconds following each pulse. This allowed for the acoustic monitoring of the fluid surface 'ring' as capillary waves reverberate from the walls of the well. The up and down motion of the fluid surface at the middle of the well is monitored and recorded. About 60 milliseconds after the application of the acoustic toneburst, 300 traces were obtained, each trace containing an echo signal from the fluid surface. Through echo correlation analysis, a time-delay value was then obtained for each echo signal.

Figure 7:
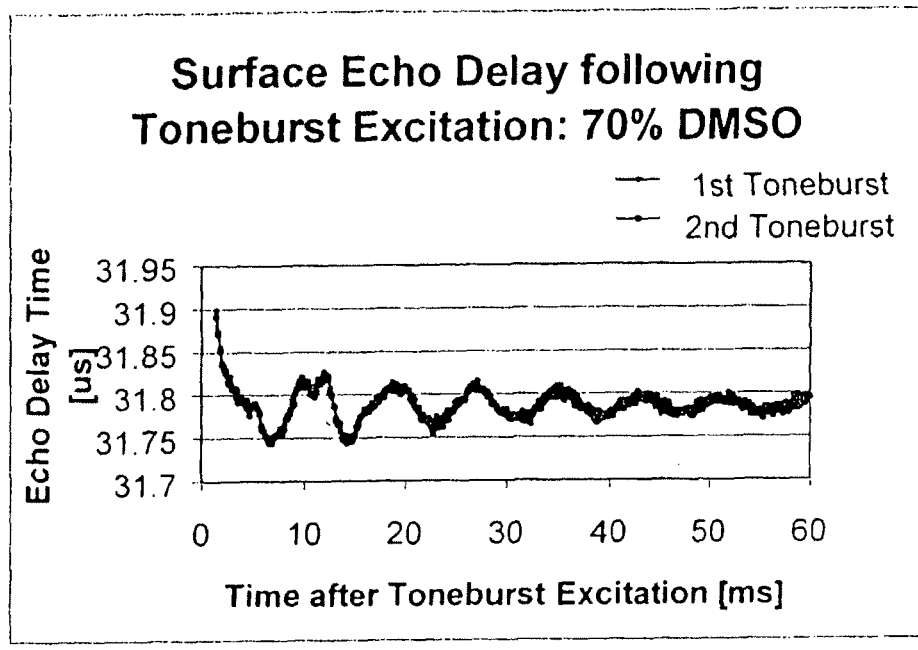
FIG. 7 is a graph that plots measured echo delay times of interrogating acoustic radiation as a function of time after a toneburst perturbs a fluid surface.

FIG. 7 is a graph that plots the measured echo delay time (round trip time of flight for a pulse from the transducer to the well fluid surface), as a function of time after the toneburst. Data from two successive measurements are shown, indicating the repeatability of the measurement. From the data contained in FIG. 7, it was found that the pulse echo signals measured in the first 1.5 milliseconds following the toneburst excitation are too different from those of a 'normal' surface echo to produce meaningful surface height information. After about 2 milliseconds, the curvature of the fluid surface is sufficiently low that the pulse echo shapes look much more like 'normal' surface reflections.

From the data contained in FIG. 7, it was determined that a change in the echo delay time of 0.1 microseconds corresponds to a change in fluid height of approximately 80 micrometers. Thus, it is evident from the data contained in FIG. 7 that after the application of the toneburst, there is an initial surface relaxation, followed by reverberation of the fluid surface. It appears that at shorter times (e.g., 10 milliseconds), capillary waves of higher spatial frequency are present, which produce the harmonic content in the fluid surface motion. By about 25 milliseconds, however, it appears that the fundamental reverberation mode is dominant. By using data from FIG. 7, fluid properties such as surface tension and viscosity may be determined. Generally, the surface tension dictates the periodicity of the signal seen in FIG. 7, and the viscosity determines the damping of the fluid surface reverberation. Depending on the time regime of interest, various analytical techniques may be used.

EXAMPLE 2

Figure 8:
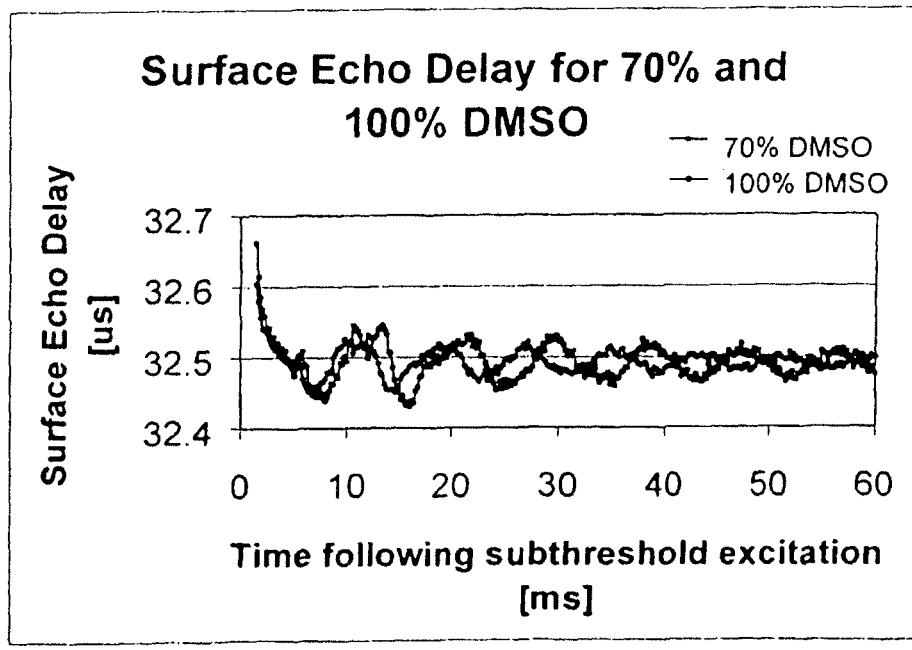
FIG. 8 is a graph that plots the measured echo delay time for two different fluids as a function of time after the toneburst perturbs the fluids' surfaces.
Figure 9A:
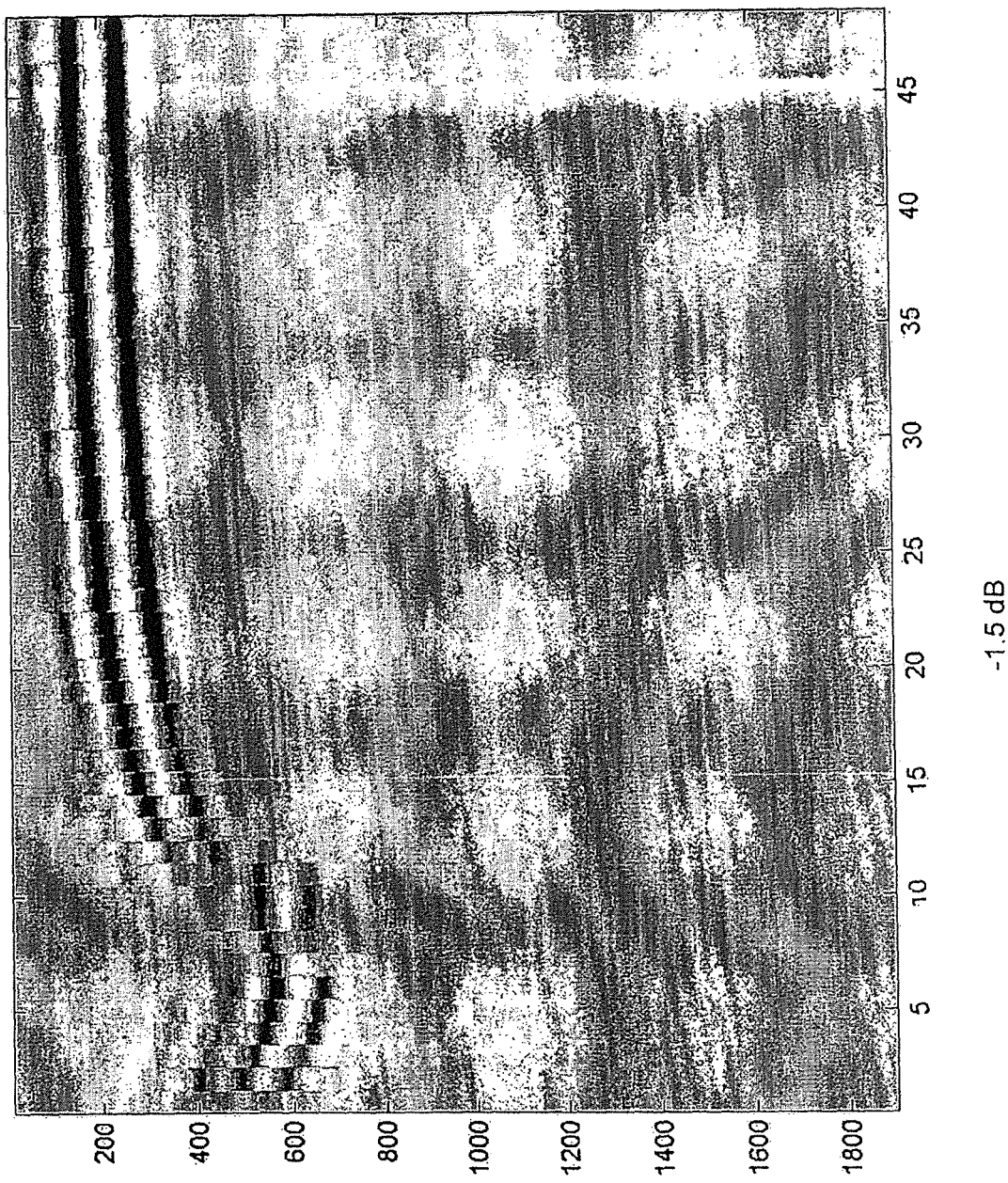
FIGS. 9A-9H depict the acoustic radiation coming into the transceiver from a series of probe pulses after the application of a test toneburst at different power levels relative to the ejection threshold.
Figure 9B:
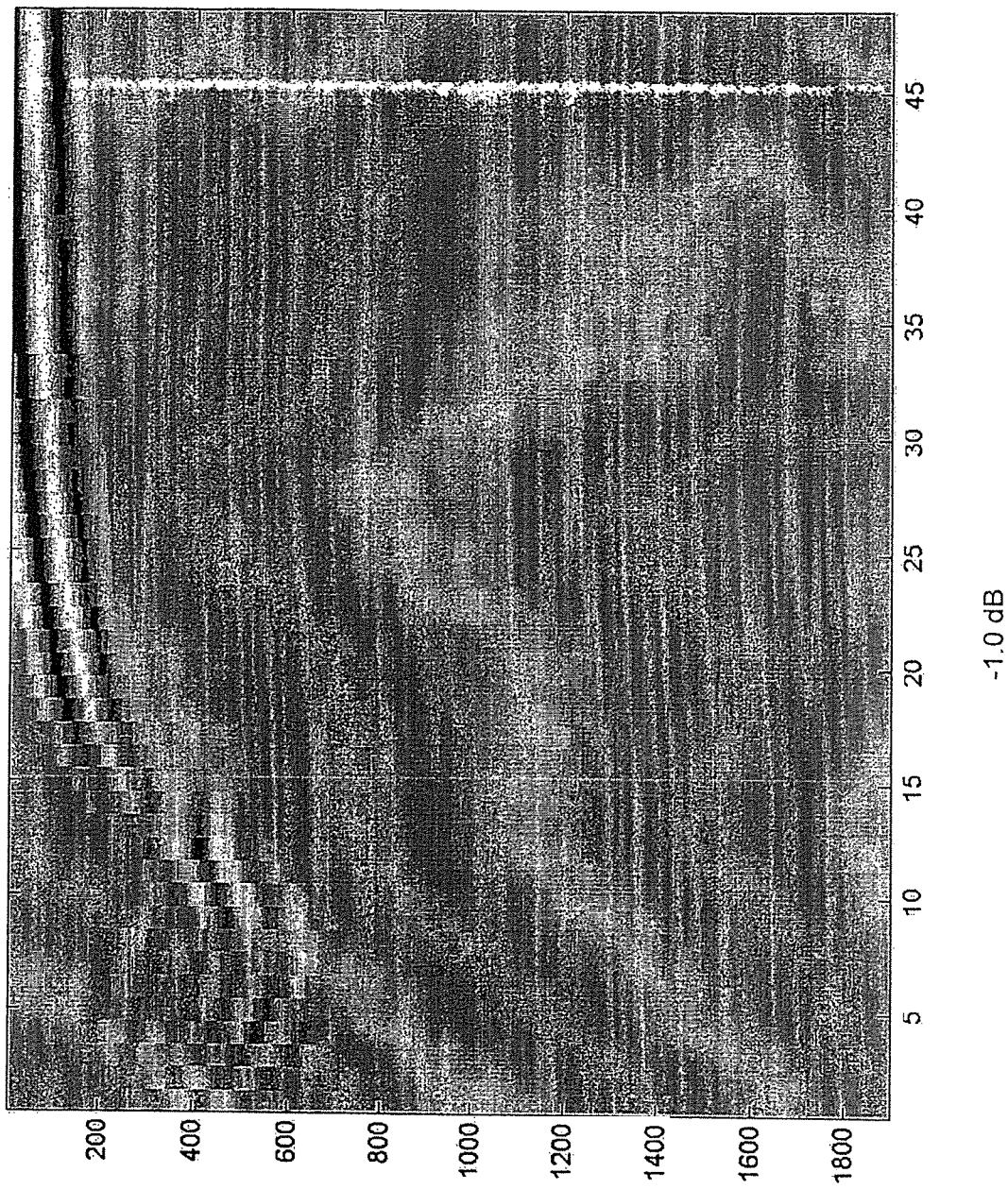
Figure 9C:
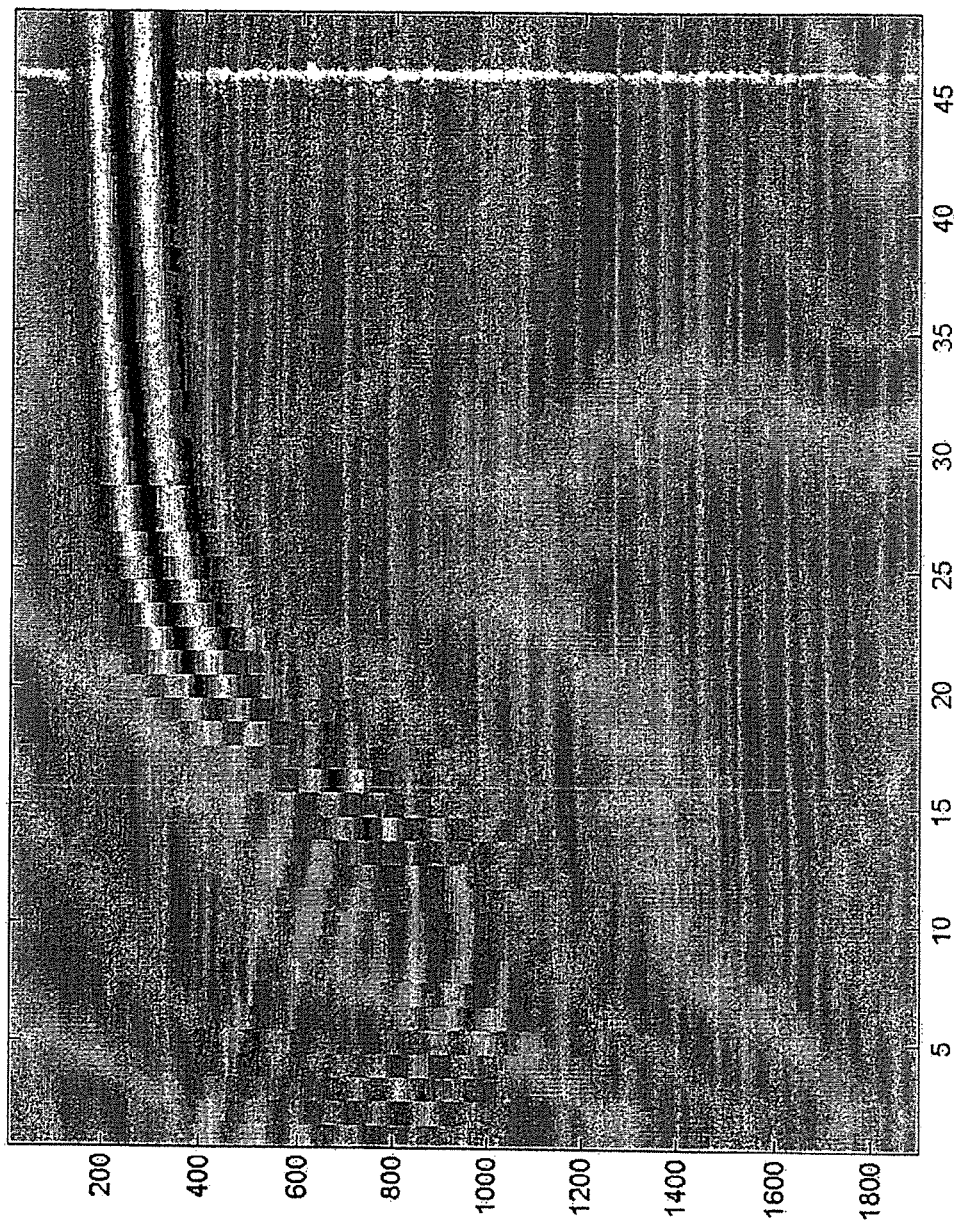
Figure 9D:
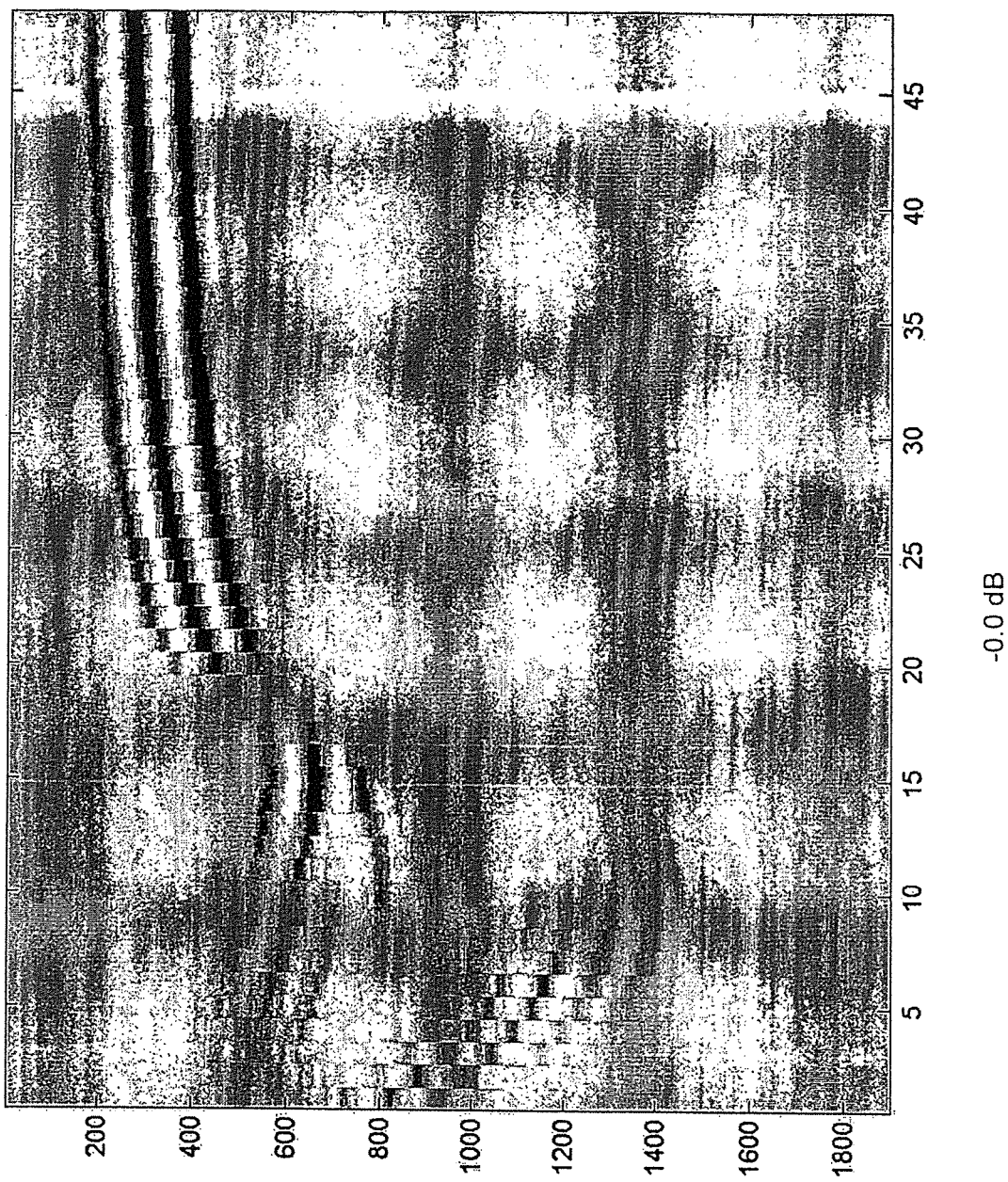
Figure 9E:
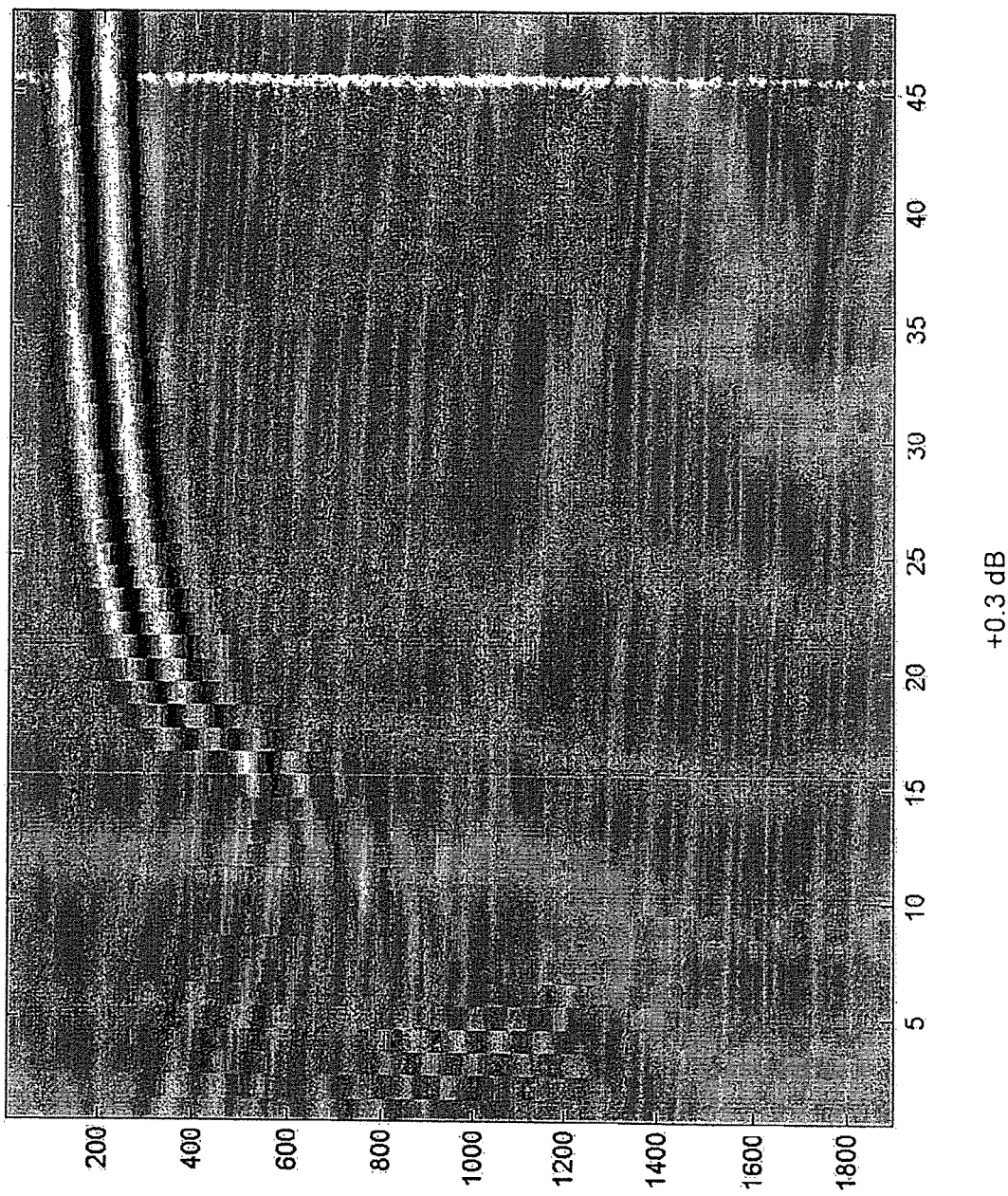
Figure 9F:
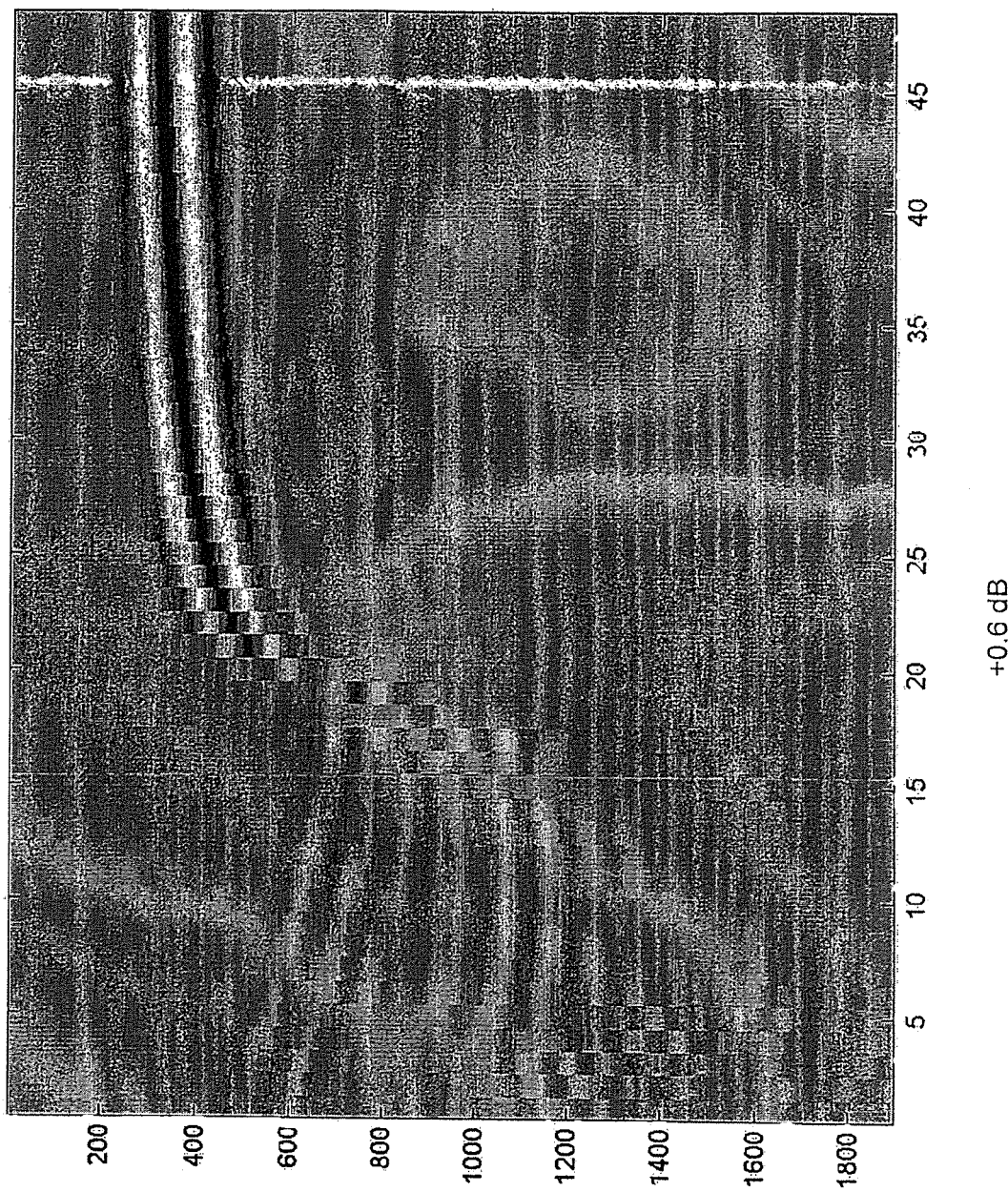
Figure 9G:
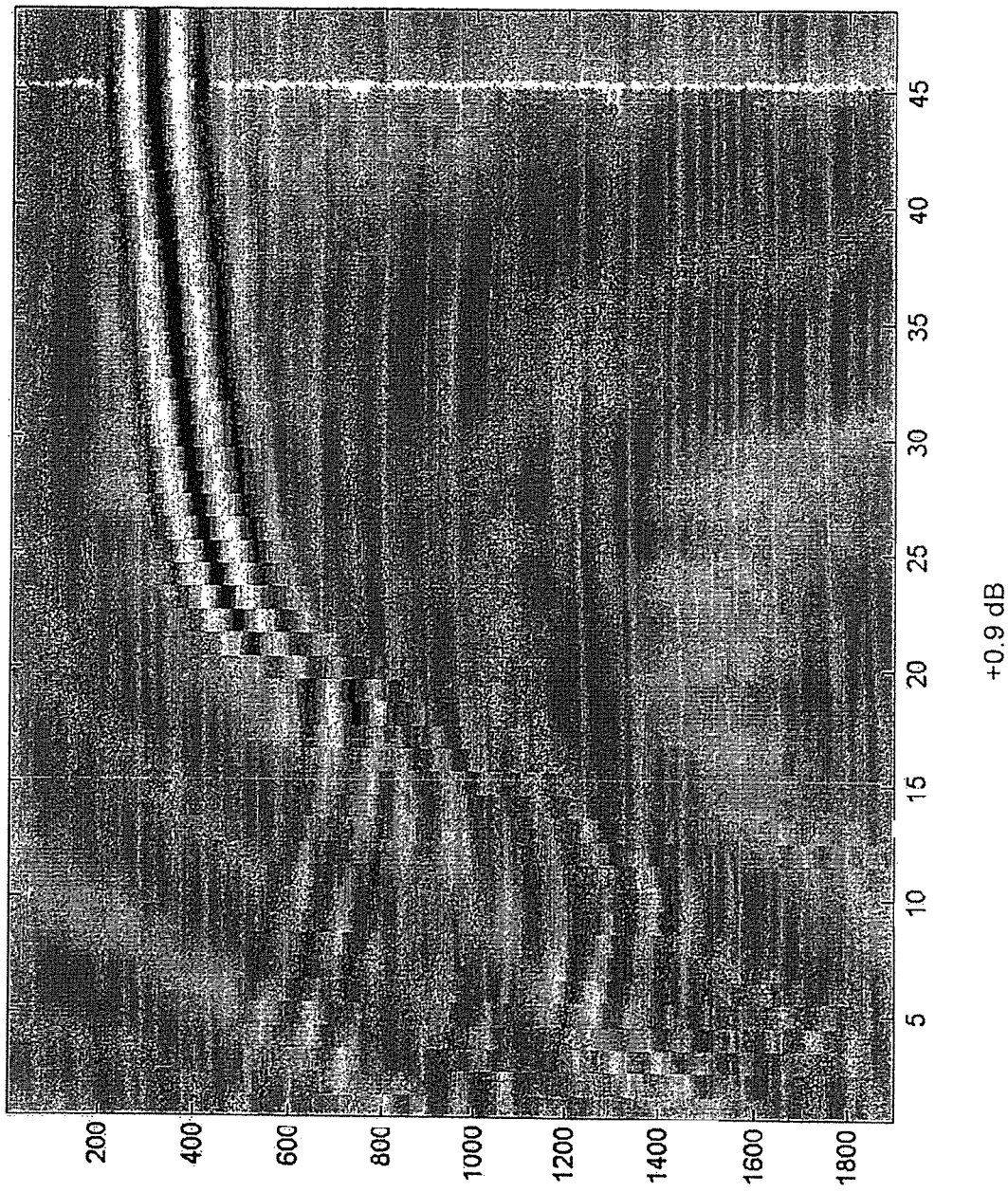
Figure 9H:
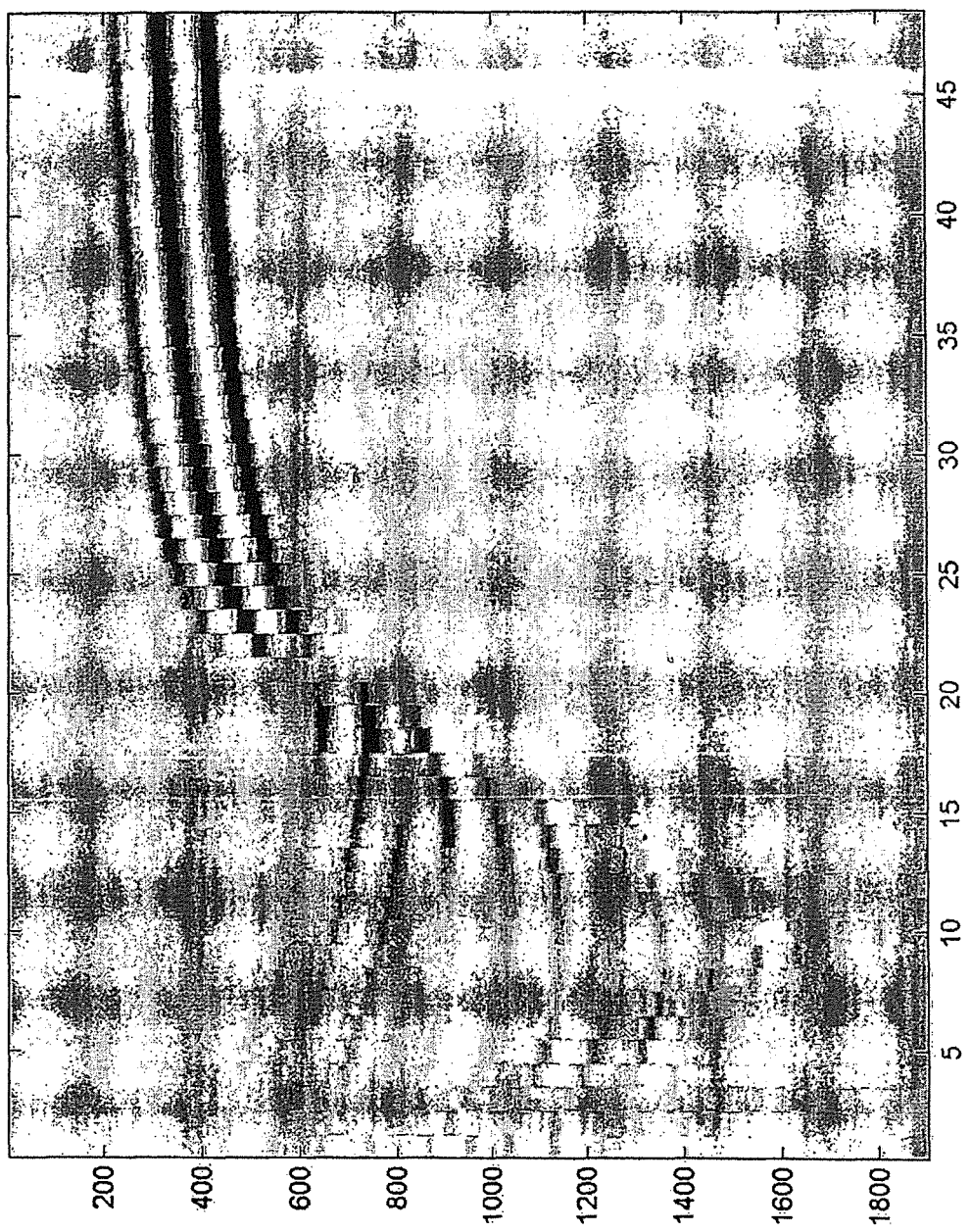

Measurements similar to those described in Example 1 were made except that a fluid containing 100% DMSO was employed in place of the solution containing 70% DMSO and 30% water. FIG. 8 is a graph that plots the measured echo delay time for this fluid as well as for the solution containing DMSO and water mixture as a function of time after the toneburst. Since optimal delay time is slightly different for the two fluids, the data for the mixture is plotted with an arbitrary offset in the vertical direction for ease in visual comparison.

The data for the two fluids were fitted to exponentially decaying sinusoidal waveforms, in the time period 25 millisecond<t<60 milliseconds following the toneburst. The surface oscillation period and exponential delay time for the fluid containing the DMSO and water mixture are 8.11 milliseconds and 27.4 milliseconds, respectively. The surface oscillation period and exponential delay time for the fluid containing the 100% DMSO are 8.98 milliseconds and 50.6 milliseconds, respectively.

Because the exponential damping time generally varies inversely with the fluid viscosity, the data for the two fluids implies that the viscosity of the DMSO and water solution is 1.82 times greater than the viscosity of the 100% DMSO fluid. This is in good agreement with the reported ratio of 1.85. Similarly, because the surface oscillation period is generally proportional to the inverse square root of the surface tension, the surface tension of the DMSO and water solution should be 1.23 times greater than that of the 100% DMSO. This also in good agreement with the reported surface tension for 100% DMSO (44 dyne/cm) and the reported surface tension for water (72 dyne/cm).

EXAMPLE 3

A well of a well plate is filled with a fluid. A transducer is aligned at approximately the center of the well, and the transducer height is optimized for ejection. A toneburst is applied to the fluid as to perturb the fluid surface and to produce a superthreshold ejection cone. As a result, a droplet is formed and separated from the ejection cone.

Before, during and after the formation of the ejection cone, a series of echo pulses is generated to monitor the perturbation of the fluid surface. As a result, the formation of the droplet is monitored through a series of such echo events.

EXAMPLE 4

A well of a well plate is filled with a fluid. A transducer is aligned at approximately the center of the well, and the transducer height is optimized for ejection. A series of tonebursts is applied to the fluid as to perturb the fluid surface and to produce an ejection cone. Immediately before, during and after the formation of the ejection cone, a series of echo pulses is generated to monitor the perturbation of the fluid surface as a result of each toneburst. As a result, the threshold for ejection is determined.

EXAMPLE 5

Wells of a 384-well polypropylene (PP) flat-bottom plate (Labcyte P/N P-05525-CV1) were filled with 50 µL of water. The plate was placed into a Labcyte® Echo™ 550 compound reformatter. A VP248 Disposable 384 Polypropylene Pin Tool, (V&P Scientific, Inc, San Diego, Calif.) modified and adapted to be held in the destination plate gripper of the Echo 550 so the instrument z-axis could be used for precise pin movements. Pins were moved in an up-down-up-down-up-down cycle, resulting in six time-of-flight measurements. Based on six values per well, the speed of sound was found to be within 0.3% of the literature value using a 1 mm motion of the pins and compensating for the focus of the transducer (F-number of 2 in water). Another microplate was prepared with 60 µL of 70% DMSO/30% water per well. With 1.5 mm pin travel, the processed data showed similar agreement and had a coefficient of variation (CV) of 0.2%.

We claim:

1. A method for determining a speed of sound in a fluid, the method comprising:
    immersing a solid object at a first location in a quantity of the fluid in a reservoir;
    sending first acoustic energy to the solid object;
    detecting second acoustic energy reflected from the solid object at the first location;
    moving the solid object from the first location to a second location in the quantity of the fluid;
    detecting third acoustic energy reflected from the solid object at the second location; and
    calculating a speed of sound in the fluid by using as an input a distance between the first location of the solid object and the second location of the solid object.

2. The method of claim 1, and further comprising generating the first acoustic energy by an acoustic ejection system capable of ejecting droplets of fluid from the reservoir.

3. The method of claim 1, wherein the solid object is a pin tool.

4. The method of claim 1, wherein the process for sending first acoustic energy to the solid object includes directing the first acoustic energy in a vertical direction towards the solid object.

5. The method of claim 1, wherein the first acoustic energy is focused and associated with an F-number.

6. The method of claim 5, wherein the F-number is approximately 2 or greater.

7. The method of claim 5, wherein the process for calculating a speed of sound in the fluid is performed by using as an input the F-number.

8. The method of claim 1, wherein the method is carried out for each of a plurality of fluids in a plurality of reservoirs respectively.

9. The method of claim 8, wherein the plurality of reservoirs for the plurality of fluids for which the method is carried out form part of a well plate.

10. A method for determining a speed of sound in a fluid, the method comprising:
    immersing a solid object in a quantity of the fluid in a reservoir;
    supplying first acoustic energy by an acoustic ejection system capable of ejecting droplets of fluid from the reservoir; and
    detecting second acoustic energy reflected from the solid object;
    wherein the process for immersing a solid object is performed by using a positioning system also used by the acoustic ejection system for other purposes.

11. The method of claim 10, and further comprising:
    moving the solid object; and
    detecting third acoustic energy reflected from the solid object in its position after being moved.

12. The method of claim 10, and further comprising calculating a speed of sound in the fluid by using as an input a distance between the solid object and a portion of the fluid in the reservoir closest to the acoustic ejection system.

13. The method of claim 10, wherein the solid object is a pin tool.

14. The method of claim 10, wherein the process for supplying first acoustic energy includes directing the first acoustic energy in a vertical direction towards the solid object.

15. The method of claim 10, wherein the method is carried out for each of a plurality of fluids in a plurality of reservoirs respectively.

16. The method of claim 15, wherein the plurality of reservoirs for the plurality of fluids for which the method is carried out form part of a well plate.

17. The method of claim 10, wherein the first acoustic energy is focused and associated with an F-number.

18. The method of claim 17, wherein the F-number is approximately 2 or greater.

19. The method of claim 17, and further comprising calculating a speed of sound in the fluid by using as an input the F-number.

* * * * *